US011040197B2

(12) United States Patent
Ludwig et al.

(10) Patent No.: US 11,040,197 B2
(45) Date of Patent: Jun. 22, 2021

(54) VOLTAMMETRIC NEUROCHEMICAL DETECTION IN WHOLE BLOOD

(71) Applicant: Mayo Foundation for Medical Education and Research, Rochester, MN (US)

(72) Inventors: Kip A. Ludwig, Rochester, MN (US); Kendall H. Lee, Rochester, MN (US); Kevin E. Bennet, Rochester, MN (US); Evan N. Nicolai, Rochester, MN (US); Anders J. Asp, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 244 days.

(21) Appl. No.: 16/014,216

(22) Filed: Jun. 21, 2018

(65) Prior Publication Data

US 2018/0369587 A1 Dec. 27, 2018

Related U.S. Application Data

(60) Provisional application No. 62/523,417, filed on Jun. 22, 2017.

(51) Int. Cl.
*A61N 1/36* (2006.01)
*G01N 27/327* (2006.01)
(Continued)

(52) U.S. Cl.
CPC ........ *A61N 1/36053* (2013.01); *A61B 5/0538* (2013.01); *A61B 5/1473* (2013.01);
(Continued)

(58) Field of Classification Search
CPC ............ G01N 27/3277; A61N 1/36053; A61N 1/0556; A61B 5/04001; A61B 5/0538;
(Continued)

(56) References Cited

U.S. PATENT DOCUMENTS 5,650,061 A 7/1997 Kuhr et al.
5,806,517 A 9/1998 Gerhardt et al.
(Continued)

FOREIGN PATENT DOCUMENTS

WO WO 2010/083208 7/2010
WO WO 2011/028608 3/2011
(Continued)

OTHER PUBLICATIONS

Abosch et al., "Stimulation of the subthalamic nucleus in Parkinson's disease does not produce striatal dopamine release," Neurosurgery, 2003, 53:1095-1102; discussion 1102-1095.
(Continued)

*Primary Examiner* — Paula J Stice
(74) *Attorney, Agent, or Firm* — Fish & Richardson P.C.

(57) ABSTRACT

Techniques are described for determining a voltammogram that characterizes a result of a fast-scan cyclic voltammetry process. The FSCV process can be performed using a sensing apparatus at least partially immersed in a volume of blood of a mammal. A system can process the voltammogram to determine a concentration of a neurochemical in the volume of blood of the mammal.

20 Claims, 13 Drawing Sheets

(51) Int. Cl.
*A61B 5/145* (2006.01)
*A61B 5/00* (2006.01)
*A61B 5/0538* (2021.01)
*A61B 5/1473* (2006.01)
*A61B 5/24* (2021.01)
*A61N 1/05* (2006.01)

(52) U.S. Cl.
CPC ............ *A61B 5/14546* (2013.01); *A61B 5/24* (2021.01); *A61B 5/4076* (2013.01); *G01N 27/3277* (2013.01); *A61B 5/7225* (2013.01); *A61N 1/0556* (2013.01)

(58) Field of Classification Search
CPC . A61B 5/14546; A61B 5/1476; A61B 5/4076; A61B 5/7225
See application file for complete search history.

(56) References Cited

U.S. PATENT DOCUMENTS

| | | | |
|---|---|---|---|
| 6,164,284 | A | 12/2000 | Schulman |
| 7,209,788 | B2 | 4/2007 | Nicolelis |
| 7,440,806 | B1 | 10/2008 | Whitehurst et al. |
| 7,747,318 | B2 | 6/2010 | John et al. |
| 7,899,545 | B2 | 3/2011 | John |
| 7,901,368 | B2 | 3/2011 | Flaherty et al. |
| 8,140,152 | B2 | 3/2012 | John et al. |
| 8,315,703 | B2 | 11/2012 | Lozano |
| 8,359,100 | B2 | 1/2013 | Cameron et al. |
| 8,433,415 | B2 | 4/2013 | Leiter et al. |
| 8,473,060 | B2 | 6/2013 | Leiter et al. |
| 9,603,522 | B2 | 3/2017 | Lee et al. |
| 9,841,403 | B2 | 12/2017 | Lee et al. |
| 10,029,101 | B2 | 7/2018 | Bennet et al. |
| 2002/0013612 | A1 | 1/2002 | Whitehurst |
| 2004/0108223 | A1 | 6/2004 | Jansson |
| 2006/0009814 | A1 | 1/2006 | Schulman |
| 2006/0173509 | A1 | 8/2006 | Lee et al. |
| 2006/0195157 | A1 | 8/2006 | Lee et al. |
| 2006/0241717 | A1 | 10/2006 | Whitehurst et al. |
| 2007/0026440 | A1 | 2/2007 | Broderick et al. |
| 2007/0100378 | A1* | 5/2007 | Maschino ............... A61N 1/32 607/2 |
| 2008/0179197 | A1 | 7/2008 | Wu |
| 2008/0258116 | A1 | 10/2008 | Viticoli et al. |
| 2008/0288023 | A1 | 11/2008 | John |
| 2010/0032316 | A1 | 2/2010 | Wu |
| 2010/0312305 | A1 | 12/2010 | Leiter et al. |
| 2012/0088983 | A1 | 4/2012 | Jung et al. |
| 2012/0165634 | A1 | 6/2012 | Lee et al. |
| 2013/0023745 | A1 | 1/2013 | Lee et al. |
| 2014/0018639 | A1* | 1/2014 | Jamieson ............. A61B 5/4848 600/301 |
| 2015/0141272 | A1* | 5/2015 | Gordon ................ C12Q 1/6804 506/9 |
| 2015/0250421 | A1* | 9/2015 | Arumugam ........ A61B 5/14865 600/345 |
| 2015/0360032 | A1 | 12/2015 | Bennet |
| 2016/0192872 | A1 | 7/2016 | Lee |
| 2018/0043162 | A1* | 2/2018 | Canning ................ A61P 11/00 |
| 2018/0296145 | A1* | 10/2018 | Shivkumar ......... A61B 5/14735 |

FOREIGN PATENT DOCUMENTS

| | | |
|---|---|---|
| WO | WO 2014/110263 | 7/2014 |
| WO | WO 2015/021470 | 2/2015 |

OTHER PUBLICATIONS

Adams, "In vivo electrochemical measurements in the CNS," Prog Neurobiol, 1990, 35(4):297-311.

Agnesi et al., "Wireless Instantaneous Neurotransmitter Concentration System-based amperometric detection of dopamine, adenosine, and glutamate for intraoperative neurochemical monitoring," J Neurosurg., 2009, 111:701-711.

Aillon et al., "Near real-time measurement of glutamate concentration changes using biosensors in place of traditional methodologies," in Phillips PEM, Sandberg SG, Ahn S, Phillips AG (ed): proceeding of the 12th international conference on in vivo methods 2008. University of British Columbia, Vancouver, Canada. 2008, pp. 108-110.

Albin et al., "The functional anatomy of basal ganglia disorders," Trends Neurosci., 1989, 12:366-375.

Anami et al., "Stepping stone sampling for retrieving artifactfree electroencephalogram during functional magnetic resonance imaging," Neuroimage, 2003, 19:281-295.

Anastassiou et al. "Subsecond voltammetric separation between dopamine and serotonin in the presence of ascorbate," Anal Chem., 78(19):6990-6998, Oct. 1, 2006.

Anderson et al., "Mechanisms of deep brain stimulation: an intracellular study in rat thalamus," J Physiol., 2004 559:301-313.

Atcherly et al., "Fast-scan controlled-adsorption voltammetry for the quantification of absolute concentrations and adsorption dynamics," ACS Langmuir, Nov. 2013, 29: 14885-14892.

Bakker and Qin, "Electrochemical sensors," Anal Chem., 2006, 78:3965-3984.

Bar-Gad et al., "Complex locking rather than complete cessation of neuronal activity in the globus pallidus of a 1-methyl-4-phenyl-1,2,3,6-tetrahydropyridine-treated primate in response to pallidal microstimulation," J Neurosci., 2004, 24:7410-7419.

Bath et al., "Subsecond Adsorption and Desorption of Dopamine at Carbon-Fiber Microelectrodes," Anal. Chem., 2000, 72:5994-6002.

Baur et al., "Fast-scan voltammetry of biogenic amines," Anal Chem., 1988, 60:1268-1272.

Bekar et al., "Adenosine is crucial for deep brain stimulation-mediated attenuation of tremor," Nat Med., 2008, 14:75-80.

Benabid et al., "Combined (thalamotomy and stimulation) stereotactic surgery of the VIM thalamic nucleus for bilateral Parkinson disease," Appl Neurophysiol., 1987, 50:344-346.

Benabid, "Deep brain stimulation for Parkinson's disease," Curr Opin Neurobiol., 2003, 13:696-706.

Benveniste, "Brain microdialysis," J Neurochem., 1989, 52:1667-1679.

Bergman et al., "Pathophysiology of Parkinson's disease: from clinical neurology to basic neuroscience and back," Mov. Disord., 2002, 17:S28-S40.

Bergman et al., "Reversal of experimental parkinsonism by lesions of the subthalamic nucleus," Science, 1990, 249:1436-1438.

Bergstrom and Garris, "Utility of a tripolar stimulating electrode for eliciting dopamine release in the rat striatum," J Neurosci. Methods, 1999, 87:201-208.

Beurrier et al., "High-frequency stimulation produces a transient blockade of voltage-gated currents in subthalamic neurons," J Neurophysiol., 2001, 85:1351-1356.

Blagoev et al., "Modelling the magnetic signature of neuronal tissue," NeuroImage, 2007, 37:137-148.

Blaha and Phillips, "A critical assessment of electrochemical procedures applied to the measurement of dopamine and its metabolites during drug-induced and species-typical behaviours," Behav Pharmacol., 1996, 7:675-708.

Blaha and Winn, "Modulation of dopamine efflux in the striatum following cholinergic stimulation of the substantia nigra in intact and pedunculopontine tegmental nucleus-lesioned rats," J. Neurosci., 1993, 13(3):1035-1044.

Blaha et al., "Modulation of Dopamine Efflux in the Nucleus Accumbens after Cholinergic Stimulation of the Ventral Tegmental Area in Intact, Pedunculopontine Tegmental Nucleus-Lesioned, and Laterodorsal Tegmental Nucleus-Lesioned Rats," J. Neurosci., 1996, 16:714-722.

Blaha et al., "Striatal dopamine release evoked by subthalamic stimulation in intact and 6-0HDA-lesioned rats: Relevance to deep brain stimulation in Parkinson's Disease," In: P. E. M. Phillips, S. G. Sandberg, S. Ahn, A. G. Phillips (Eds.), Monitoring Molecules in Neuroscience. University of British Columbia, Vancouver, BC, 2008, pp. 395-397.

(56) References Cited

OTHER PUBLICATIONS

Bledsoe et al., "Development of the Wireless Instantaneous Neurotransmitter Concentration System for intraoperative neurochemical monitoring using fast-scan cyclic voltammetly," J Neurosurg., 2009, 111(4):712-723.
Bledsoe et al., "MRI compatible stereotaxic head-frame and navigation software for research in pigs," Neuroscience, 2008, Program#/Poster#: 695.8/UU92, 2 pages.
Bonmassar et al., "Visual evoked potential (VEP) measured by simultaneous 64-channel EEG and 3T fMRI," Neuroreport, 1999, 10:1893-1897.
Borland and Michael, "An introduction to electrochemical methods in neuroscience," in Michael AC, Borland LM (ed): Electrochemical Methods for Neuroscience. Boca Raton: CRC Press, 2007, 10 pages.
Borland et al., "Voltammetric study of extracellular dopamine near microdialysis probes acutely implanted in the striatum of the anesthetized rat," J Neurosci Methods, 2005, 146:149-158.
Breit et al., "Deep brain stimulation," Cell Tissue Res, 2004, 318:275-288.
Brown and Pilitsis, "Motor cortex stimulation for central and neuropathic facial pain: a prospective study of 10 patients and observations of enhanced sensory and motor function during stimulation," Neurosurg., 2005, 56:290-297; discussion 290-297.
Bruet et al., "High frequency stimulation of the subthalamic nucleus increases the extracellular contents of striatal dopamine in normal and partially dopaminergic denervated rats," J Neuropathol Exp Neurol., 2001, 60:15-24.
Bruet et al., "Neurochemical mechanisms induced by high frequency stimulation of the subthalamic nucleus: increase of extracellular striatal glutamate and GABA in normal hemiparkinsonian rats," J Neuropathol Exp Neurol., 2003, 62:1228-1240.
Burmeister et al., "Advances in the in vivo detection of GABA using enzyme coated microelectrode arrays," in Phillips PEM, Sandberg SG, Ahn S, Phillips AG (ed): proceeding of the 12th international conference on In Vivo methods 2008. University of British Columbia, Vancouver, Canada. 2008, p. 111-113.
Burmeister et al., "Improved ceramic-based multisite microelectrode for rapid measurements of L-glutamate in the CNS," J Neurosci Methods, 2002, 119:163-171.
Busenbark et al., "Accuracy of reported family histories of essential tremor," Neurology, 1996, 47:264-265.
Cahill et al., "Microelectrodes for the measurement of catecholamines in biological systems," Anal Chem., 1996, 68(18):3180-3186.
Carmichael et al., "Functional MRI with active, fully implanted, deep brain stimulation systems: Safety and experimental confounds," NeuroImage, 2007, 37:508-517.
Cavus et al., "Decreased hippocampal volume on MRI is associated with increased extracellular glutamate in epilepsy patients," Epilepsia, 2008, 49:1358-1366.
Cechova and Venton, "Transient adenosine efflux in the rat caudate-putamen," J Neurochem., 2008, 105:1253-1263.
Chang et al., "Studies of the neural mechanisms of deep brain stimulation in rodent models of Parkinson's disease," Neurosci Biobehav Rev., 2008, 32:352-366.
Childs et al., "Vagus Nerve Stimulation as a Tool to Induce Plasticity in Pathways Relevant for Extinction Learning," J Visualized Exper, 2015, e53032, 12 pages.
Chow et al., "Delay in vesicle fusion revealed by electrochemical monitoring of single secretory events in adrenal chromaffin cells," Nature, 1992, 356(6364):60-63.
Clapp-Lilly et al., "An ultrastructural analysis of tissue surrounding a microdialysis probe," J Neurosci Methods, 1999, 90:129-142.
Covey et al., "Monitoring subthalamic nucleus-evoked dopamine release in the striatum using fast-scan cyclic voltammetry in vivo," in P.E.M. Phillips (Eds), Monitoring Molecules in Neuroscience. University of British Columbia, Vancouver, BC, 2008, 398-400.
Crespi et al., "In vivo voltammetry: from wire to wireless measurements," J Neurosci Methods, 2004, 140(1-2):153-61.

Cumming et al., "Kinetics of the uptake and distribution of the dopamine D(2,3) agonist (R)-N-[1-(11)C]n-propylnorapomorphine in brain of healthy and MPTP-treated Gottingen miniature pigs," Nucl Med Biol., 2003, 30:547-553.
Dale et al., "Listening to the brain: microelectrode biosensors for neurochemicals," Trends Biotechnol., 2005, 23:420-428.
Dale et al., "Rapid adenosine release in the nucleus tractus solitarii during defense response in rats: real-time measurement in vivo," J Physiol., 2002, 544(Pt 1):149-160.
Dall et al., "Quantitative [18F]fluorodopa/PET and histology of fetal mesencephalic dopaminergic grafts to the striatum of MPTP-poisoned minipigs," Cell Transplant., 2002, 11:733-746.
Danielsen et al., "The DaNeX study of embryonic mesencephalic, dopaminergic tissue grafted to a minipig model of Parkinson's disease: preliminary findings of effect of MPTP poisoning on striatal dopaminergic markers," Cell Transplant., 2000, 9:247-259.
Dobbing, "The influence of early nutrition on the development and myelination of the brain," Proc Royal Soc Lond B Biol Sci., 1964, 159:503-509.
Dommett et al., "How visual stimuli activate dopaminergic neurons at short latency," Science, 2005, 307:1476-1479.
Dostrovsky et al., "Microstimulation-induced inhibition of neuronal firing in human globus pallidus," J Neurophysiol., 2000, 84:570-574.
Dugast et al., "Continuous in vivo monitoring of evoked dopamine release in the rat nucleus accumbens by amperometry," Neuroscience, 1994, 62:647-654.
Dunn et al., "Functional Brian Mapping at 9.4T Using a New MRI-Compatible Electrode Chronically Implanted in Rats," Magnetic Resonance Med., 2009, 61:222-228.
Eccles et al., Pulse Cyclic Voltammetry.II. Flowing Solutions, Canadian J Chem., 65(8):1795-1799, Aug. 1, 1987.
European Communication pursuant to Article 94(3) EPC, dated Mar. 6, 2017, 5 pages.
European Search Report in the European Application No. 14834533.3, dated Feb. 17, 2017, 4 pages.
Fedele et al., "Microdialysis in Parkinsonian patient basal ganglia. acute apomorphine-induced clinical and electrophysiological effects not paralleled by changes in the release of neuroactive amino acids," Exp Neurol., 2001, 167:356-365.
Felix et al., "Stereotaxic atlas of the pig brain," Brain Res Bull., 1999, 49:1-137.
Forster and Blaha, "Pedunculopontine tegmental stimulation evokes striatal dopamine efflux by activation of acetylocholine and glutamate receptors in the midbrain and pons of the rat," Eur. J. Neurosci., 2003, 17:751-762.
Frank et al., "Hold your horses: impulsivity, deep brain stimulation, and medication in parkinsonism," Science, 2007, 318:1309-1312.
Garcia et al., "Dual effect of high-frequency stimulation on subthalamic neuron activity," J Neurosci., 2003, 23:8743-8751.
Garcia et al., "High-frequency stimulation in Parkinson's disease: more or less?" Trends Neurosci., 2005, 28:209-216.
Garguilo and Michael, "Amperometric microsensors for monitoring choline in the extracellular fluid of brain," J Neurosci Methods, 1996, 70:73-82.
Garris et al., "Dissociation of dopamine release in the nucleus accumbens from intracranial self-stimulation," Nature, 1999, 398(6722):67-9.
Garris et al., "Dopamine release and uptake both decrease in the partially denervated striatum in proportion to the loss of dopamine terminals," Brain Res., 1997, 753(2):225-34.
Garris et al., "In vivo voltammetry with telemetry," in Michael AC, Borland LM (ed): Electrochemical Methods for Neuroscience. Boca Rhaton: CRC Press, 2007, pp. 233-259.
Garris et al., "Real-time measurement of electrically evoked extracellular dopamine in the striatum of freely moving rats," J Neurochem., 1997, 68:152-161.
Garris et al., "Wireless transmission of fast-scan cyclic voltammetry at a carbon-fiber microelectrode: proof of principle," J Neurosci Methods, 2004, 140(1-2):103-115.
Gerhardt, "Rapid chronocoulometric measurements of norepinephrine overflow and clearance in CNS tissues," Neuromethods: voltam-

(56) References Cited

OTHER PUBLICATIONS metric methods in brain systems, ed. G.B. A Boulton, RN Adams. 1995, Totowa, NJ: Human Press Inc. 117-51.
Gourine et al., "Adenosine release in nucleus tractus solitarii does not appear to mediate hypoxia-induced respiratory depression in rats," J Physiol., 2002, 544:161-70.
Graybiel, "Neurotransmitters and neuromodulators in the basal ganglia," Trends Neurosci, 1990, 13:244-254.
Greene, "Deep-brain stimulation for generalized dystonia," N Engl J Med, 2005, 352:498-500.
Groh and Ney, "Anesthesia for magnetic resonance imaging," Curr Opin Anaethesiol., 1997, 10:303-308.
Halassa et al., "Astrocytic Modulation of Sleep Homeostasis and Cognitive Consequences of Sleep Loss," Neuron, 2009, 61:213-219.
Hardesty and Sackeim, "Deep brain stimulation in movement and psychiatric disorders," Biol Psychiatry, 2007, 61:831-835.
Hardman et al., "Comparison of the Basal Ganglia in Rats, Marmosets, Macaques, Baboons, and Humans: Volume and Neuronal Number for the Output, Internal Relay and Striatal Modulating Nuclei," J Camp. Neural., 2002, 445:238-255.
Hascup et al., "Determining the source of resting and physiologically-evoked L-glutamate levels using enzyme-based microelectrode arrays in awake rats," in Phillips PEM, Sandberg SG, Ahn S, Phillips AG (ed): proceeding of the 12th international conference on in vivo methods 2008. University of British Columbia, Vancouver, Canada. 2008, pp. 164-167.
Hascup et al., "Second-by second measures of L-glutamate and other neurotransmitter using enzyme based microelectrode arrays," in Micheal AC, Borland LM (ed): Electrochemical methods for neuroscience. CRC. 2006, 47 pages.
Heien et al., "Overoxidation of carbon-fiber microelectrodes enhances dopamine adsorption and increases sensitivity," Analyst, Dec. 2003, 128: 1413-1419.
Heien et al., "Resolving neurotranmitters detected by fast-scan cyclic voltammetry," Ana chem, Oct. 2004, 76: 5697-5704.
Henderson and Lad, "Motor cortex stimulation and neuropathic facial pain," Neurosurg Focus, 2006, 21:E6, 4 pages.
Herzog et al., "Most effective stimulation site in subthalamic deep brain stimulation for Parkinson's disease," Mov. Disord., 2004, 19:1050-1054.
Hilker et al., "Deep brain stimulation of the subthalamic nucleus does not increase the striatal dopamine concentration in parkinsonian humans," Mov Disord, 2003, 18:41-48.
Hinman et al., "Alterations in glutamate neurotransmission after traumatic brain injury: Study using enzyme-based microelectrode arrays," in Phillips PEM, Sandberg SG, Ahn S, Phillips AG (ed): proceeding of the 12th international conference on in vivo methods 2008. University of British Columbia, Vancouver, Canada. 2008, p. 372-374.
Hubble et al., "Deep brain stimulation for essential tremor," Neurol., 1996, 46:1150-1153.
Huffman and Venton, "Carbon-fiber microelectrodes for in vivo applications," Analyst., 2009, 134:18-24.
Hurley et al., "What has been learnt from study of dopamine receptors in Parkinson's disease?" Pharmacol. Ther., 2002, 111:715-728.
Hyland et al., "Firing modes of midbrain dopamine cells in the freely moving rat," Neurosci., 2002, 114:475-492.
International Preliminary Report on Patentability for PCT/US2014/010882, dated Jul. 23, 2015, 6 pages.
International Preliminary Report on Patentability for PCT/US2014/050550, dated Feb. 18, 2016, 6 pages.
International Preliminary Report on Patentability in International Application No. PCT/US2010/046807, dated Mar. 8, 2012, 6 pages.
International Search Report and Written Opinion for PCT/US2014/10882, dated Apr. 4, 2014, 12 pages.
International Search Report and Written Opinion for PCT/US2014/50550 dated Nov. 20, 2014, 10 pages.
International Search Report and Written Opinion in International Application No. PCT/US2010/046807, dated May 31, 2011, 9 pages.
Jackson et al., "Fast-scan cyclic voltammetry of 5-hydroxytryptamine," Anal Chem., 1995, 67:1115-1120.
Jang et al. "Paired pulse voltammetry for differentiating complex analytes," Analyst. 137(6):1428-1435, Epub Feb. 2, 2012.
Jaquins-Gerstl and Michael, "Comparison of the brain penetration injury associated with microdialysis and voltammetry," J Neurosci Methods, 2009, 183:127-135.
Justice et al., "Voltammetry in the neuroscience," Clifton, NJ. Humana Press, 1987, 395 pages.
Kagohashi et al., "Wireless voltammetry recording in unanesthetised behaving rats," Neurosci Res., 2008, 60:120-127.
Kawagoe et al., "pH-Dependent processes at Nafion-coated carbon-fiber microelectrodes," J Electroanal Chem., 1993, 359:193-197.
Keeler et al., "Accessory equipment considerations with respect to MRI compatibility," J Magn Reson Imaging, 1998, 8:12-18.
Keithly and Wightman, "Assessing principal component regression prediction of neurochemicals detected with fast-scan cyclic voltammetry," ACS Chem Neurosci, Jun. 2011, 2: 514-525.
Keithly et al., "Higher sensitivity dopamine measurements with faster-scan cyclic voltammetry," Anal Chem, May 2011, 83: 3563-3571.
Kern and Kumar, "Deep brain stimulation," Neurologist, 2007, 13:237-252.
Kimble et al., "Wireless Instantaneous Neurotransmitter Concentration Sensing System (WINCS) for Intraoperative Neurochemical Monitoring," 31st Annual International Conference of the IEEE EMBS, 2009, 4 pages.
Kishida et al., "Subsecond dopamine fluctuations in human Striatum encode superposed error signals about actual and counterfactual reward," PNAS, Jan. 2016, 113: 200-205.
Kita and Kitai, "Efferent Projections of the Subthalamic Nucleus in the Rat: Light and Electron Microscopic Analysis with the PHA-L Method," J Camp. Neural., 1987, 260:435-452.
Konradsson et al., "Second-by-second measurement of stimulated glutamate release and its modulation by $\alpha 7$ and mGlu 2/3 receptors: relevance to schizophrenia," in Phillips PEM, Sandberg SG, Ahn S, Phillips AG (ed): proceeding of the 12th international conference on in vivo methods 2008. University of British Columbia, Vancouver, Canada. 2008, pp. 123-126.
Krakow, "Imaging epileptic activity using functional MRI," Neurodegener Dis, 2008, 5:286-295.
Kristensen and Wightman, "Dispersion in flow injection analysis measured with microvoltammetric electrodes," Anal Chem, 1986, 58:986-988.
Kulagina et al., "Monitoring glutamate and ascorbate in the extracellular space of brain tissue with electrochemical microsensors," Anal Chem., 1999, 71:5093-5100.
Lane, "Differential double pulse voltammetry at chemically modified platinum electrodes for in vivo determination of catechol amines," Analytical Chemistry, 48(9):1287-1293, Aug. 1976.
Lee et al, "Evolution of Deep Brain Stimulation. Human Electrometer and Smart Devices Supporting the Next Generation of Therapy," Neuromodulation: Technology at the Neural Interface, 2009, 12(2):85-103.
Lee et al., "Dopamine efflux in the rat striatum evoked by electrical stimulation of the subthalamic nucleus: potential mechanism of action in Parkinson's disease," Eur. J. Neurosci., 2006, 23:1005-1014.
Lee et al., "Effect of High-Frequency Stimulation of the Subthalamic Nucleus on Subthalamic Neurons: An Intracellular Study," Stereotactic. Funct. Neurasurg., 2003, 80:32-36.
Lee et al., "High-frequency stimulation of the subthalamic nucleus increases glutamate in the subthalamic nucleus of rats as demonstrated by in vivo enzyme-linked glutamate sensor," Brain Res., 2007, 1162:121-129.
Lee et al., "Neurotransmitter release from high-frequency stimulation of the subthalamic nucleus," J Neurosurg., 2004, 101:511-517.
Limberger et al., "'Real time' measurement of endogenous dopamine release during short trains of pulses in slices of rat neostriatum and

(56) References Cited

OTHER PUBLICATIONS nucleus accumbens: role of autoinhibition," Naunyn-Schmiedeberg's Arch Pharmacol., 1991, 344:623-629.
Limousin et al., "Electrical stimulation of the subthalamic nucleus in advanced Parkinson's disease," N Engl J Med, 1998, 339:1105-1111.
Lind et al., "Mapping the amphetamine-evoked dopamine release in the brain of the Göttingen minipig," Brain Res Bull., 2005, 65:1-9.
Lind et al., "The use of pigs in neuroscience: modeling brain disorders," Neurosci Biobehav Rev, 2007, 31(5):728-51.
Littlewood et al., "Mapping the central effects of ketamine in the rat using pharmacological MRI," Psychopharmacology (Berl), 2006, 186:64-81.
Llaudet et al., "A three-enzyme microelectrode sensor for detecting purine release from central nervous system," Biosens Bioelectron., 2003, 18:43-52.
Logothetis et al., "Neurophysiological investigation of the basis of the fMRI signal," Nature, 2001, 412:150-157.
Lowry and Fillenz, "Real-time monitoring of brain energy metabolism in vivo using microelectrochemical sensors: the effects of anesthesia," Bioelectrochem., 2001, 54:39-47.
Lowry eta l., "An amperometric glucose-oxidase/poly(o-phenylenediamine) biosensor for monitoring brain extracellular glucose: in vivo characterization in the striatum of freely-moving rats," J Neurosci Methods, 1998, 79:65-74.
Lozano et al., "Subcallosal cingulate gyrus deep brain stimulation for treatment-resistant depression," Biol Psychiatry, 2008, 64:461-467.
Maarrawi et al., "Motor cortex stimulation for pain control induces changes in the endogenous opioid system," Neurol., 2007, 69:827-834.
Macmillan et al., "Accuracy of a miniature intracranial pressure monitor, its function during magnetic resonance scanning, and assessment of image artifact generation," Neurosurgery, 1999, 45:188-192.
Mandelkow et al., "Synchronization facilitates removal of MRI artefacts from concurrent EEG recordings and increases usable bandwidth," Neuroimage, 2006, 32-1120-1126.
Mayberg et al., "Deep brain stimulation for treatment-resistant depression," Neuron, 2005, 45:651-660.
Mazzone et al., "Implantation of human pedunculopontine nucleus: a safe and clinically relevant target in Parkinson's disease," Neuroreport, 2005, 16:1877-1881.
McIntyre et al., "Uncovering the mechanism(s) of action of deep brain stimulation: activation, inhibition, or both," Clin Neurophysiol., 2004, 115:1239-1248.
Meissner et al., "Deep brain stimulation in late stage Parkinson's disease: a retrospective cost analysis in Germany," J Neurol. 2005, 252:218-223.
Meissner et al., "Deep brain stimulation of subthalamic neurons increases striatal dopamine metabolism and induces contralateral circling in freely moving 6-hydroxydopamine-lesioned rats," Neurosci Lett., 2002, 328:105-108.
Meissner et al., "Striatal dopaminergic metabolism is increased by deep brain stimulation of the subthalamic nucleus in 6-hydroxydopamine lesioned rats," Neurosci Lett., 2001, 303:165-168.
Meltzer et al., "Modulation of dopamine neuronal activity by glutamate receptor subtypes," Neurosci. Biobehav. Rev., 1997, 21:511-518.
Menon et al., "Combined event-related fMRI and EEG evidence for temporal-parietal cortex activation during target detection," Neuroreport, 1997, 8:3029-3037.
Michael et al., "Improving data acquisition for fast-scan cyclic voltammetry," Anal Chem., 1999, 71(18):3941-3947.
Mikkelsen et al., "MPTP-induced Parkinsonism in minipigs: A behavioral, biochemical, and histological study," Neurotoxicol Teratol, 1999, 21(2):169-75.
Mitchell, "Acetylcholine and choline amperometric enzyme sensors characterized in vitro and in vivo," Anal Chem., 2004, 76:1098-106.
Molina et al., "Additive Differential pulse voltammetry, instead of double differential pulse voltammetry," Electrochem. Commun., 2001, 3:324-329.
Molinuevo et al., "Levodopa withdrawal after bilateral subthalamic nucleus stimulation in advanced Parkinson disease," Arch Neurol., 2000, 57:983-988.
Moro et al., "Chronic subthalamic nucleus stimulation reduces medication requirements in Parkinson's disease," Neurol., 1999, 53:85-90.
Moro et al., "The Impact on Parkinson's disease of electrical parameter settings in STN stimulation," Neurology, 2002, 59:706-713.
Moyer et al., "Effects of dopaminergic modulation on the integrative properties of the ventral striatal medium spiny neuron," J Neurophysiol., 2007, 98:3731-3748.
Nandi et al., "Exploration of the role of the upper brainstem in motor control," Stereotact Funct Neurosurg, 2002, 78(3-4):158-167.
Naylor et al., "A new technique for the simultaneous recording of electroencephalograph activity and CNS biosensor data," in Phillips PEM, Sandberg SG, Ahn S, Phillips AG (ed): proceeding of the 12th international conference on in vivo methods 2008. University of British Columbia, Vancouver, Canada. 2008, pp. 127-129.
Netchiporouk et al., "Brain extracellular glucose assessed by voltammetry throughout the rat sleep-wake cycle," Eur J Neurosci., 2001, 13:1429-1434.
Niazy et al., "Removal of FMRI environment artifacts from EEG data using optimal basis sets," Neuroimage, 2005, 28:720-737.
Nicolai et al., "Detection of Norepinephrine in Whole Blood via Fast Scan Cyclic Voltammetry," IEEE International Symposium on Medical Measurements and Applications, May 2017, 111.
Nicolai et al., "Electrochemical Method for Vagus Nerve Stimulation Evoked Catecholamine Release at End Organs," Minnesota Neuromodulation Symposium: Book of Abstracts, Apr. 13-14, 2017, retrieved on Sep. 18, 2018, URL <http://neuromodulation.umn.edu/doc/MNS2017ProgramAndAbstracts.pdf>, 1 page.
Nicolai et al.[Poster], "Measurement of Norepinephrine via Fast Scan Cyclic Voltammetry in Whole Blood: Biomarkers for Closing the Loop in Bioelectronics Medicine," Mayo Foundation for Medicinal Education and Research, 2016, 1 page.
Nomoto et al., "The metabolic rate and vulnerability of dopaminergic neurons, and adenosine dynamics in the cerebral cortex, nucleus accumbens, caudate nucleus, and putamen of the common marmoset," J Neural., 2000, 247:16-22.
Norris, "Principles of magnetic resonance assessment of brain function," J Magn Reson Imaging, 2006, 23:794-807.
Office action in U.S. Appl. No. 13/392,387, dated Sep. 29, 2015, 9 pages.
Office Action in U.S. Appl. No. 13/555,965, dated Aug. 13, 2015, 9 pages.
Office Action in U.S. Appl. No. 13/555,965, dated Feb. 12, 2015, 8 pages.
Office Action in U.S. Appl. No. 14/760,011, dated Dec. 4, 2015, 9 pages.
Office action in U.S. Appl. No. 13/392,387, dated Jul. 13, 2016, 19 pages.
Office action in U.S. Appl. No. 13/555,965, dated Sep. 1, 2016, 10 pages.
Office Action in U.S. Appl. No. 14/760,011, dated Jun. 16, 2016, 8 pages.
Patel et al., "Unilateral subthalamotomy in the treatment of Parkinson's disease," Brain, 2003, 126:1136-1145.
Paul et al., "High frequency stimulation of the subthalamic nucleus influences striatal dopaminergic metabolism in the naive rat," Neuroreport, 2000, 11:441-444.
Perea and Araque, "Astrocytes potentiate transmitter release at single hippocampal synapses," Science, 2007, 317:1083-1086.
Phillips et al., "Parkinson disease: pattern of functional MR imaging activation during deep brain stimulation of subthalamic nucleus—initial experience," Radiology, 2006, 239:209-216.
Pohlmeyer et al., "Toward the Restoration of Hand Use to a Paralyzed Monkey: Brain-Controlled Functional Electrical Stimulation of Forearm Muscles," PLoS ONE, 2009, 4(6):1-8.

(56) References Cited

OTHER PUBLICATIONS

Pomerleau et al., "Real time in vivo measures of L-glutamate in the rat central nervous system using ceramic-based multisite microelectrode arrays," Ann N Y Acad Sci., 2003, 1003:454-7.
Priori et al., "Do intraoperative microrecordings improve subthalamic nucleus targeting in stereotactic neurosurgery for Parkinson's disease?" J Neurosurg Sci., 2003, 47:56-60.
Purdon et al., "An open-source hardware and software system for acquisition and real-time processing of electrophysiology during high field MRI," J Neurosci Methods, 2008, 175:165-186.
Purdon et al., "Simultaneous electroencephalography and functional magnetic resonance imaging of general anesthesia," Ann N Y Acad Sci., 2009, 1157:61-70.
Rehncrona et al., "Long-term efficacy of thalamic deep brain stimulation for tremor: double-blind assessments," Mov Disord., 2003, 18:163-170.
Ren et al., "Dopaminergic response to graded dopamine concentration elicited by four amphetamine doses," Synapse, 2009, 63:764-772.
Roberts and Mikulis, "Neuro MR: principles," J Magn Reson Imaging, 2007, 26:823-837.
Robinson et al., "Detecting Subsecond Dopamine Release with Fast-Scan Cyclic Voltammetry in Vivo," Clin. Chem., 2003, 49:1763-1773.
Robinson et al., "Monitoring rapid chemical communication in the brain," Chem Rev., 2008, 108:2554-2584.
Roham et al., "Diamond microelectrodes and CMOS microelectronics for wireless transmission of fast-scan cyclic voltammetry," Conf Proc IEEE Eng Med Biol Soc, 2007. 2007::6044-7.
Saint-Cyr et al., "Localization of clinically effective stimulating electrodes in the human subthalamic nucleus on magnetic resonance imaging," J. Neurosurg., 2002, 97:1152-1166.
Sandberg and Garris, "Neurochemistry of addiction: monitoring essential neurotransmitters of addiction," in Koob GF, Kuhn C (ed): Novel Approaches to Addiction Boca Raton: CRC Press, 2010, 30 pages.
Saunders et al., "Microdialysis in nonhuman Primates," Curr Protoc Neurosci, 2001, Chapter 7:Unit7, 20 pages.
Schwarz et al., "Concurrent pharmacological MRI and in situ microdialysis of cocaine reveal relationship between the central hemodynamic response and local dopamine concentration," Neuroimage, 2004, 23:296-304.
Shastry, "Parkinson disease: etiology, pathogenesis and future of gene therapy," Neurosci. Res., 2001, 41:5-12.
Shimo and Wichmann, "Neuronal activity in the subthalamic nucleus modulates the release of dopamine in the monkey striatum," Eur. J Neurosci., 2009, 29:104-113.
Shon et al., "Comonitoring of adenosine and dopamine using the Wireless Instantaneous Neurotransmitter Concentration System: proof of principle: Laboratory investigation," J Neurosurg., 2010, 112(3):539-548.
Siniaia et al., "Habituation and desensitization of the Hering-Breuer reflex in rat," J Phys, 2000, 479-491.
Stefurak et al., "Deep brain stimulation for Parkinson's disease dissociates mood and motor circuits: a functional MRI case study," Mov Disord, 2003, 18:1508-1516.
Suaud-Chagny et al., "Uptake of dopamine released by impulse flow in the rat mesolimbic and striatal systems in vivo," J Neurochem., 1995, 65:2603-2611.
Suaud-Chagny, "In vivo monitoring of dopamine overflow in the central nervous system by amperometric techniques combined with carbon fibre electrodes," Methods., 2004, 33:322-329.
Swamy et al., "Subsecond Detection of Physiological Adenosine Concentrations Using Fast-Scan Cyclic Voltammetry," Anal. Chem., 2007, 79:744-750.
Takmakov et al., "Carbon microelectrodes with a renewable surface," ACS Anal Chem, Feb. 2010, 82: 2020-2028.
Tawfik et al., "Deep Brain Stimulation Results in Local Glutamate and Adenosine Release" Investigation into the Role of Astrocytes, Neurosurgery, 2010, 67:367-75.
Thobois et al., "Chronic subthalamic nucleus stimulation and striatal D2 dopamine receptors in Parkinson's disease—A [(11)C]-raclopride PET study," J Neurol., 2003, 250:1219-1223.
Tsubokawa et al., "Chronic motor cortex stimulation for the treatment of central pain," Acta Neurochir Suppl (Wien), 1991, 52:137-139.
Tsubokawa et al., "Chronic motor cortex stimulation in patients with thalamic pain," J Neurosurg., 1993, 78:393-401.
U.S. Appl. No. 61/358,512, filed Jun. 25, 2010, 51 pages.
Van der Zeyden et al., "Microdialysis of GABA and glutamate: analysis, interpretation and comparison with microsensors," Pharmacol Biochem Behav., 2008, 90:135-147.
Venton et al., "Real-time decoding of dopamine concentration changes in the caudate-putamen during tonic and phasic firing," J Neurochem, 2003, 87:1284-1295.
Voges et al., "Bilateral high-frequency stimulation in the subthalamic nucleus for the treatment of Parkinson disease: correlation of therapeutic effect with anatomical electrode position," J. Neurosurg., 2002, 96:269-279.
Volkmann, "Deep brain stimulation for the treatment of Parkinson's disease," J Clin Neurophysiol., 2004, 21:6-17.
Watson et al., "In vivo measurements of neurotransmitters by microdialysis sampling," Anal Chem, 2006, 78:1391-1399.
Welter et al., "Effects of high-frequency stimulation on subthalamic neuronal activity in parkinsonian patients," Arch Neurol., 2004, 61:89-96.
Wiedemann et al., "Strategies for Low Detection Limit Measurements with Cyclic Voltammetry," Anal. Chem., 1991, 63:2965-2970.
Wightman et al., "Temporally resolved catecholamine spikes correspond to single vesicle release from individual chromaffin cells," Proc Natl Acad Sci USA, 1991, 88:10754-10758.
Williams and Millar, "Concentration-dependent actions of stimulated dopamine release on neuronal activity in rat striatum," Neuroscience, 1990, 39(1):1-16.
Williams and Millar, "Differential Actions of Endogenous and Iontophoretic Dopamine in Rat Striatum," Eur J Neurosci, 1990, 2(7):658-661.
Wilson and Gifford, "Biosensors for real-time in vivo measurements," Biosens Bioelectron., 2005, 20:2388-2403.
Windels et al., "Effects of high frequency stimulation of subthalamic nucleus on extracellular glutamate and GABA in substantia nigra and globus pallidus in the normal rat," Eur J Neurosci., 2000, 12:4141-4146.
Wu et al., "Determination of release and uptake parameters from electrically evoked dopamine dynamics measured by real-time voltammetry," J Neurosci Methods, 2001, 112:119-133.
Zhao et al., "Long term high frequency stimulation of STN increases dopamine in the corpus striatum of hemiparkinsonian rhesus monkey," Brain Res., 2009, 1286:230-238.

\* cited by examiner

VOLTAMMETRIC NEUROCHEMICAL DETECTION IN WHOLE BLOOD

CROSS-REFERENCE TO RELATED APPLICATIONS

This application claims the benefit of U.S. Provisional Application Ser. No. 62/523,417, filed Jun. 22, 2017. The disclosure of the prior application is considered part of (and is incorporated by reference in) the disclosure of this application.

BACKGROUND

Bioelectric Medicines is an emerging field that capitalizes on minimally-invasive technology to stimulate the autonomic nervous system in order to evoke therapeutic biomolecular changes at the end-organ.

SUMMARY

This specification generally discloses systems, methods, devices, and other techniques for estimating the level of a neurotransmitter in blood. In some implementations, a system determines a concentration of an analyte of interest, e.g., norepinephrine, in whole blood of a mammal or other animal using a fast-scan cyclic voltammetry process performed in vivo, e.g., in a blood vessel of the mammal downstream or otherwise near an organ that produces the analyte of interest such as norepinephrine. The estimated or measured level of analyte can then be provided to a bioelectric stimulus system and used to vary parameters of a bioelectric stimulus to the mammal. The estimated or measured level of a neurochemical or other analyte can additionally or alternatively be used to determine an optimal implant placement of a stimulating device of the bioelectric stimulus system. In some implementations, the system determines a concentration of an analyte of interest in other bodily fluids such as cerebral spinal fluid.

Some implementations of the subject matter disclosed herein include a computer-implemented method that includes actions of obtaining, by a system of one or more computers, a voltammogram that characterizes a result of a fast-scan cyclic voltammetry process that was performed using a sensing apparatus at least partially immersed in a volume of blood of a mammal; and processing the voltammogram to determine a concentration of a neurochemical in the volume of blood of the mammal. The neurochemical can be norepinephrine in some examples.

Some implementations of the subject matter disclosed here include a method having actions of inserting a sensing apparatus in a blood vessel of a mammal; performing a fast-scan cyclic voltammetry process using the sensing apparatus in the blood vessel of the mammal; determining a cyclic voltammogram that characterizes a result of the fast-scan cyclic voltammetry process; processing the cyclic voltammogram to determine a concentration of a neurochemical in blood transported within the blood vessel of the mammal; and applying a bioelectric stimulus to the mammal, wherein parameters of the stimulus are based on the concentration of the neurochemical in the blood transported within the blood vessel of the mammal.

Various features and advantages of the techniques disclosed herein will be recognized by one of ordinary skill in the art in light of this description, the claims, drawings, and the entire disclosure.

DESCRIPTION OF DRAWINGS

FIG. 6A shows background CVs for TBS and blood after approximately 15 minutes of continuous application of FSCV in each solution.

FIGS. 7A and 7C (left panels) are background CVs zoomed into the voltage range surrounding the oxidation potential for each solution recorded at the beginning and the end of a 3 minute recording. FIGS. 7B and 7D (right panels) are background subtracted cyclic voltammograms (BSCVs) collected for 0.1, 0.5, and 1 uM of norepinephrine (NE). FIGS. 7A and 7B represent data collected in TBS. FIGS. 7C and 7D represent data collected in blood.

FIG. 9A shows a representative CFM before FSCV in any solution. FIG. 9B shows the representative CFM after FSCV use in blood for 15 minutes. Scale bars are 20 micrometers.

Like references and indicators among the drawings indicate like elements.

DETAILED DESCRIPTION

In general, measuring the level of a neurochemical in blood of a mammal, especially whole blood such as blood transported within a blood vessel, involves challenges that are not present when measuring the level of an analyte in a buffer solution, due at least in part to electrode biofouling that results when a measurement electrode is placed in a blood-based solution for an extended period of time. Some implementations of the techniques disclosed herein may, in some instances, permit reliable measurements of neurochemical levels in whole blood and may at least partially overcome the effects of biofouling for electrodes used in fast-scan cyclic voltammetry measurements in blood.

Figure 1:
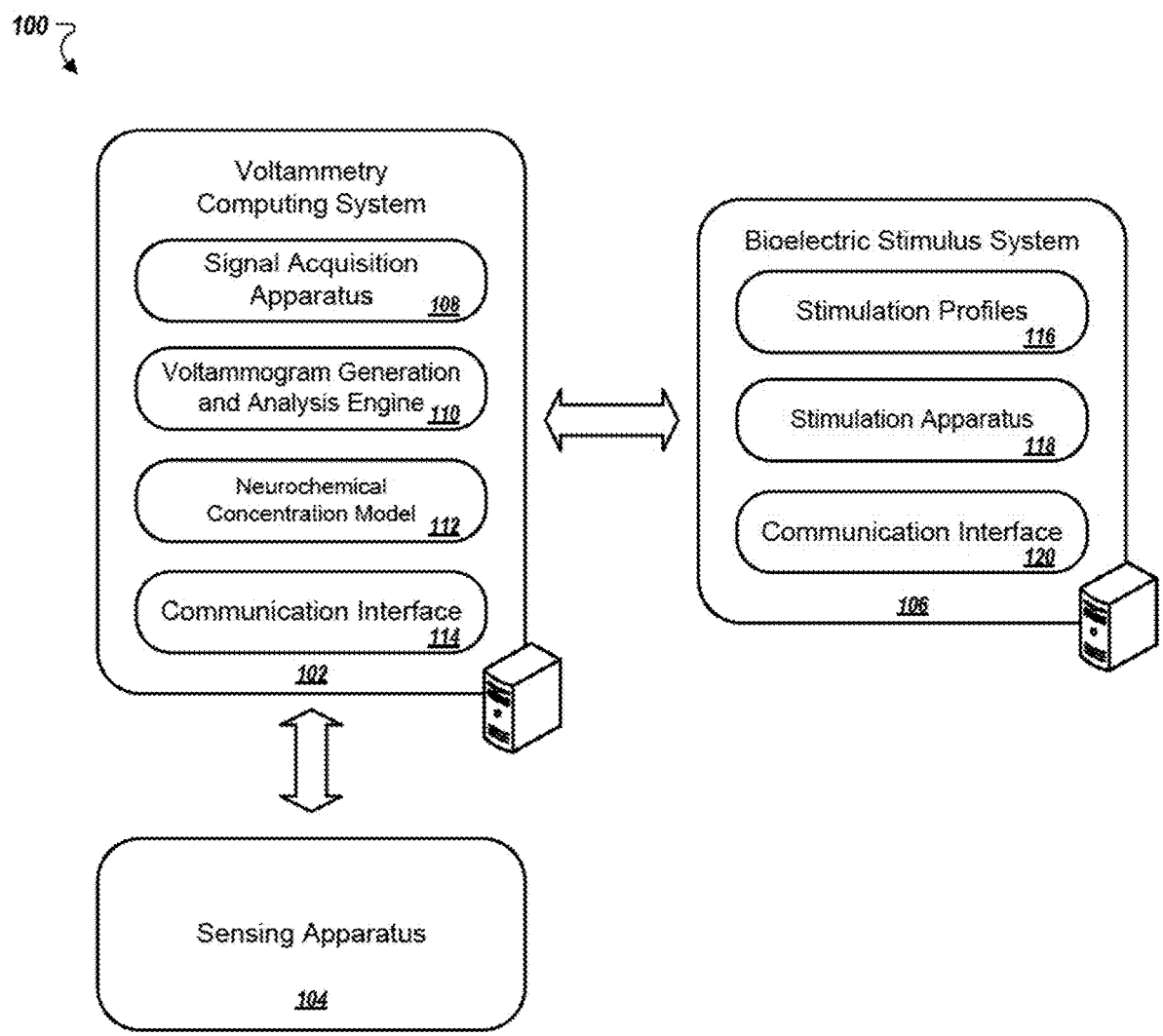
FIG. 1 is a conceptual diagram illustrating an example environment for measuring a level of an electroactive neurochemical in blood of a mammal and controlling an electrical stimulus applied to the mammal based on the measured level of neurochemical

Referring to FIG. 1, an example environment 100 is illustrated for measuring a level of an electroactive neurochemical in blood of a mammal and controlling an electrical stimulus applied to the mammal based on the measured level of neurochemical. The environment 100 includes a voltammetry computing system 102, a sensing apparatus 104, and a bioelectric stimulus system 106.

The sensing apparatus 104 is configured to perform a voltammetry process to obtain data that can be used to estimate the level of an electroactive neurochemical in blood of a mammal. In some implementations, the sensing apparatus 104 is configured to perform fast-scan cyclic voltammetry in order to provide high-temporal resolution of measurements over an extended period of time. For example, using fast-scan cyclic voltammetry, measurements can frequently and periodically be taken of the level of a neurochemical in a volume of blood over an extended length of time so that the neurochemical level can be identified at particular times and changes in the level may be observed over the extended length of time.

Figure 2:
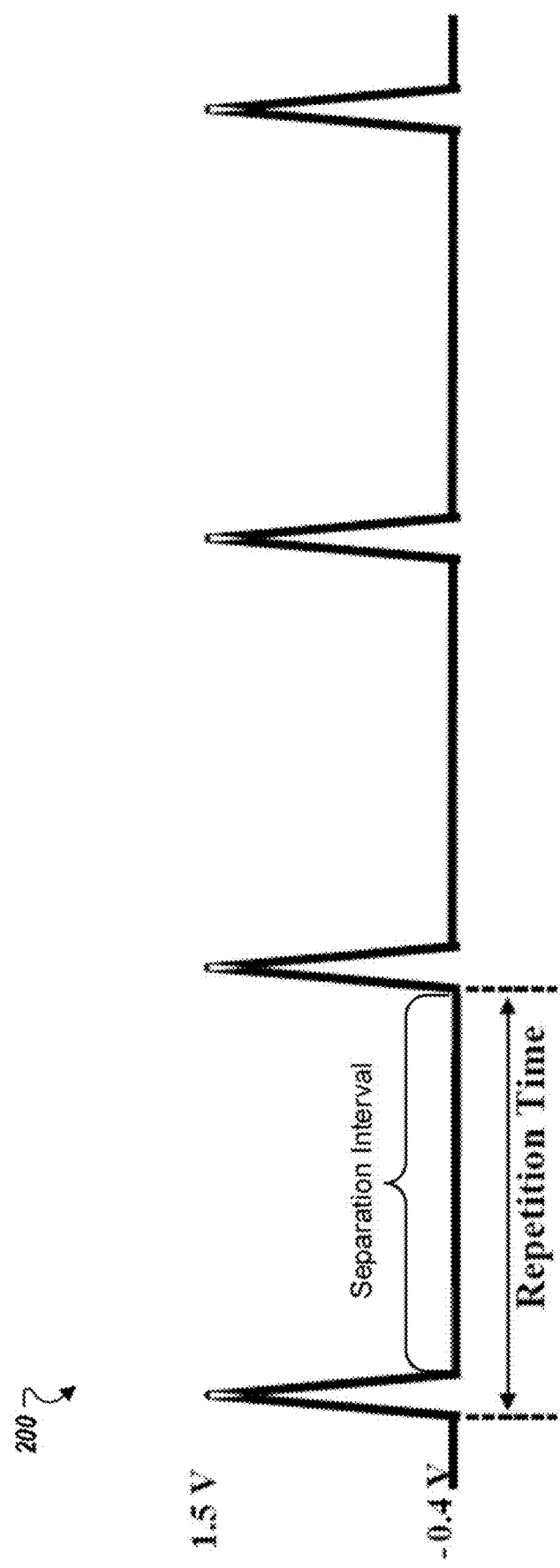
FIG. 2 is a diagram of an example waveform for an applied voltage between a working and reference electrode during a fast-scan cyclic voltammetry process.

The sensing apparatus 104 can include one or more electrodes that are configured to be at least partially immersed in a volume or sample of blood in order to facilitate measurement of neurochemical levels in the blood. In some implementations, the sensing apparatus 104 includes a working electrode, a reference electrode, and a counter electrode. All three electrodes may be placed in the blood during a voltammetry process. For in vivo measurements in blood, in some implementations the reference electrode and the counter electrode coupled together into one unit. The electrodes may be minimally invasive and delivered to a targeted site using a stiff catheter or needle. A flexible carbon fiber microelectrode may be stiffened with an agent that loses stiffness in the body to facilitate delivery of the electrodes to the targeted site. The agent can include, for example, polyethylene glycol, hyaluronic acid, and/or a stiff polymer that upon hydration becomes soft and pliable without dissolving. For example, the sensing apparatus 104 may include a signal generator that applies and varies an electrical voltage between the working electrode and reference electrode, and may further include an electrical current detector that measures the electrical current from the working electrode to the counter electrode as the voltage is varied between the working and reference electrodes. In some implementations, a tip of the working electrode is made of carbon fiber and has a diameter in the range of 1 micron to 1000 microns, and preferably has a diameter of 7 microns. In some implementations, the length of the tip of the working electrode is in the range 5 to 5000 microns, and preferably has a length of 100 microns. In some implementations, the length of the tip of the working electrode is in the range 0 microns (for a disc) to 200 microns. In some implementations, the tip of the working electrode is made of graphene, boron-doped diamond, polypyrrole, polyethylenedioxythiphene (PEDOT) and pyrolized carbon, diamond-like carbon (DLC), carbon nanotubes (CNT), carbon nanotube yarns, silicon carbide, or glassy carbon. Any of these electrode materials may be coated with an insulating material such as borosilicate glass, polyamide, epoxy, pdms, or silicone. The electrode may additionally or alternatively be coated with Nafion or platinum black. During fast-scan cyclic voltammetry, the signal generator repeatedly ramps up and down the applied voltage between a lower voltage level limit and an upper voltage level limit. An example waveform of voltages applied during a fast-scan cyclic voltammetry process is depicted in FIG. 2.

The voltammetry computing system 102 is configured to receive signals from the sensing apparatus 104 and to process the signals to determine levels of one or more analytes in a solution, e.g., a concentration of norepinephrine or other electroactive neurochemical in whole blood of a mammal. The concentration of other neurochemicals that can be measured include, for example, acetylcholine, dopamine, 5-HT, adenosine, serotonin (GI), epinephrine, oxygen, pH, DOPAC, cytosine, guanine, thyamine, NADH, and NAD. The computing system 102 may be implemented as one or more computers in one or more locations. For example, the computing system 102 may be a desktop computer, notebook computer, smartphone, microcomputer, application-specific integrated circuit (ASIC), tablet computing device, smart watch, or other mobile or wearable computing device. In other implementations, the computing system 102 may be implemented on one or more server computers that provide a cloud-based service for analyzing voltammetry data and determining levels of neurochemicals or other analytes in solution.

The voltammetry computing system 102 can include a signal acquisition apparatus 108, a voltammogram generation and analysis engine 110, a neurochemical concentration model 112, and a communication interface 114.

The signal acquisition apparatus 108 is configured to receive signals from the sensing apparatus 104 that characterize a voltammetry process, e.g., a fast-scan cyclic voltammetry process, performed by the sensing apparatus 104. The signal acquisition apparatus 108 may process the received signals to generate voltammetry data that can be processed by the voltammogram generation and analysis engine 110. For example, the sensing apparatus 104 may generate an analog signal that corresponds to a level of electrical current sensed in a solution in which electrodes of the sensing apparatus 104 are located. The signal acquisition apparatus 108 may sample and quantize the analog signal to generate digital voltammetry data, and may perform other pre-processing or signal conditioning operations such as filtering or amplifying the signal to remove noise. In some implementations, leads from the sensing apparatus 104 may be physically connected to the signal acquisition apparatus 108 to permit the apparatus 108 to capture voltammetry signals from the sensing apparatus 104. In other implementations, the sensing apparatus 104 wirelessly transmits voltammetry signals to the signal acquisition apparatus 108, e.g., over a short-range wireless network such as BLUETOOTH or WI-FI (IEEE 802.11).

The voltammogram generation and analysis (VGA) engine 110 is configured to process voltammetry data provided by the signal acquisition apparatus 108. In some implementations, the VGA engine 110 generates a voltammogram from the voltammogram data, where the voltammogram characterizes a result of a voltammetry process performed by the sensing apparatus 104. A voltammogram is a collection of empirical data that indicates levels of electrical current in a solution during a voltammetry process as the voltage applied in the solution is varied. In some implementations, a voltammogram is plotted to show electrical current as a function of voltage applied in a solution.

Figure 5C:
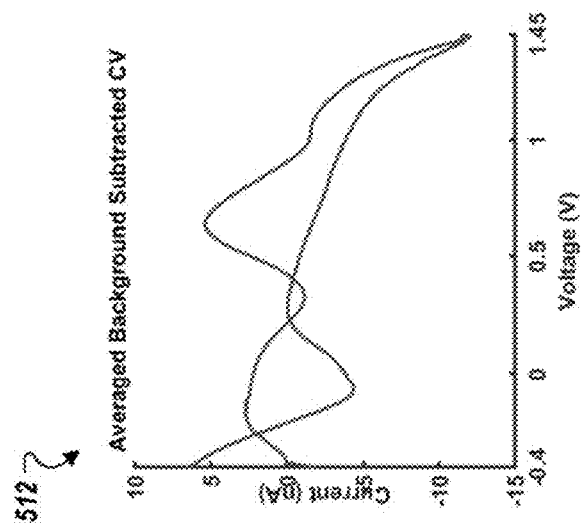
FIGS. 5A-5E show a series of voltammogram plots that can be generated and analyzed by a voltammetry computing system to estimate a level of neurochemical in a volume of blood of a mammal.
Figure 5B:
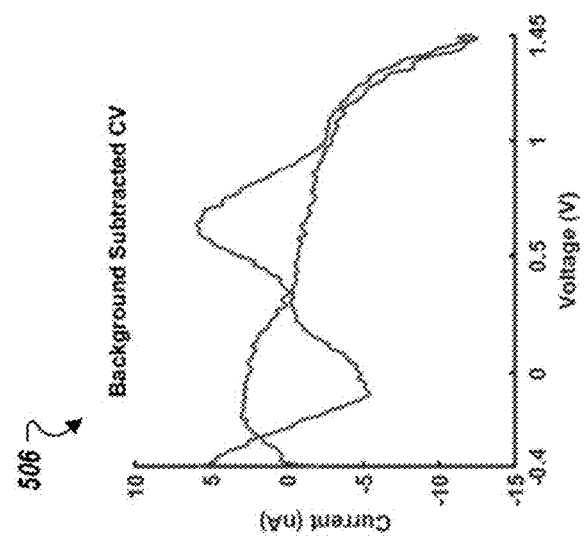
Figure 5A:
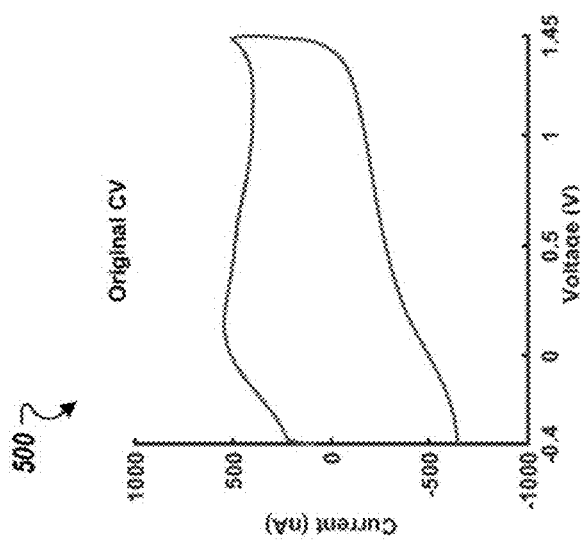

FIG. 5A, for example, shows a plotted voltammogram for a representative cycle of a fast-scan cyclic voltammetry process. In fast-scan cyclic voltammetry, the applied electrical potential (voltage) is ramped up and down again, but the resulting electrical current exhibits hysteresis, such that the electrical current for a given voltage depending on whether the voltage is being increased or decreased. During use as a feed back device, the voltammogram can be virtual, in computer memory, or a vector matrix rather than as a plotted function.

The VGA engine 110 is also configured to analyze and determine features of a voltammogram that can be used to estimate a level of a neurochemical in whole blood or other solutions. In some implementations, the VGA engine 110 determines a peak electrical current in the voltammgram for an oxidation or reduction phase, or determines an area of a peak oxidation or reduction wave in the voltammogram, or both. Further detail for determination of these features is described with respect to FIG. 4, for example.

The voltammetry computing system 102 can also include a neurochemical concentration model 112. The neurochemical concentration model 112 models relationships between one or more voltammogram features and levels of analytes in solution, e.g., concentrations of norepinephrine or other neurochemicals in whole blood of a mammal. In some implementations, the neurochemical concentration model 112 is configured to receive data indicating values of one or more features of a voltammogram and to output an indication of a concentration of the neurochemical based on the values of the one or more features of the voltammogram. In some implementations, the model 112 is a linear model derived using logistic regression or other techniques based on one or more experiments that correlated voltammogram feature values with neurochemical concentrations in blood. The model 112 may be generally applicable to a population of patients or other mammals, or may be personalized to one or more particular patients or mammals. In some implementations, the model 112 may be a trained artificial neural network.

In some implementations, the voltammetry computing system 102 includes a communication interface 114 to communicate over a physical link or a wireless link with a bioelectric stimulus system 106. The bioelectric stimulus system 106 is configured to apply an electrical stimulus to one or more parts of a mammal, e.g., a human. In some implementations, the bioelectric stimulus system 106 uses minimally invasive techniques to stimulate the autonomic nervous system of a mammal in order to evoke therapeutic biomolecular changes at an end organ of the mammal. For example, the system may apply electrical stimulation to the vagus nerve of a mammal to trigger an autonomic nervous system response. To improve the efficacy of autonomic nerve stimulation, and to facilitate continuous titration of therapy for an extended length of time, the bioelectric stimulus system 106 may rely on feedback from one or more biomarkers of the mammal to monitor the efficacy of stimulation and adjust the stimulation according to certain criteria. One such biomarker that the bioelectric stimulus system 106 may monitor is the concentration of norepinephrine, and/or other electroactive neurochemicals, in blood of the mammal. For example, electrodes of the sensing apparatus 104 may be placed in a blood vessel of the mammal at or near the targeted end organ so that the concentration of norepinephrine can be monitored in real-time during titration of bioelectric therapy. The electrodes of the sensing apparatus 104 may additionally or alternatively be placed in a blood vessel of the mammal at or near an organ that secretes the neurochemical (e.g., norepinephrine), so that the neurochemical is more concentrated and requires less sensitivity in the detection systems. The bioelectric stimulus system 106 can adjust the parameters of bioelectric stimulus applied to the mammal based on the concentration of norepinephrine and/or other neurochemicals in blood transported within the blood vessel where the electrodes are located.

In some implementations, the bioelectric stimulus system 106 includes a memory that stores a set of stimulation profiles 116, a stimulation apparatus 118, and a communication interface 120. The stimulation profiles 116 each indicate a respective set of parameters for bioelectric stimulus to apply to the mammal for a given set of biomarkers or other conditions. The stimulation apparatus 118 can include a power source, signal generator, electrodes, and other components to apply a stimulus according to a selected stimulation profile 116. The communication interface 120 is configured to receive, and optionally transmit, data to the voltammetry computing system 102 over a physical or wireless link. For example, the values of one or more voltammogram features determined by the voltammetry computing system 102 may be received at the bioelectric stimulus system 106 via the communication interface 120.

FIG. 2 is a diagram of an example waveform 200 for an applied voltage between a working and reference electrode during a fast-scan cyclic voltammetry process. The waveform 200 includes a series of voltammetry cycles in which the voltage is repeatedly ramped up and down between a lower voltage and an upper voltage. In the example shown in FIG. 2, the voltage is varied from a lower voltage (base potential) of −0.4 V to an upper voltage (peak potential) of +1.5 V. Other voltage ranges may also apply. For example, the base potential and upper potential may be any potentials within the range −3 V to +3V. During a first phase of each cycle, the voltage can be increased, e.g., linearly, from the lower to the upper voltage. During a second phase of each cycle, the voltage can be decreased, e.g., linearly, from the upper to the lower voltage. In some implementations, a separation interval provides a delay between the end of the second phase of a cycle and the beginning of the first phase of the next cycle. In other implementations, no separation interval may be provided between phases of successive cycles. Other waveforms are also possible in a fast-scan cyclic voltammetry process. In some implementations the repetition frequency of voltammgram cycles is in the range 0.1 to 100 Hz, and is preferably in the range 1 to 60 Hz or 1 to 10 Hz. In some implementations, a paired-pulse fast-scan cyclic voltammetry may be used in order to discriminate further among neurochemicals and ions in solution.

Figure 3:
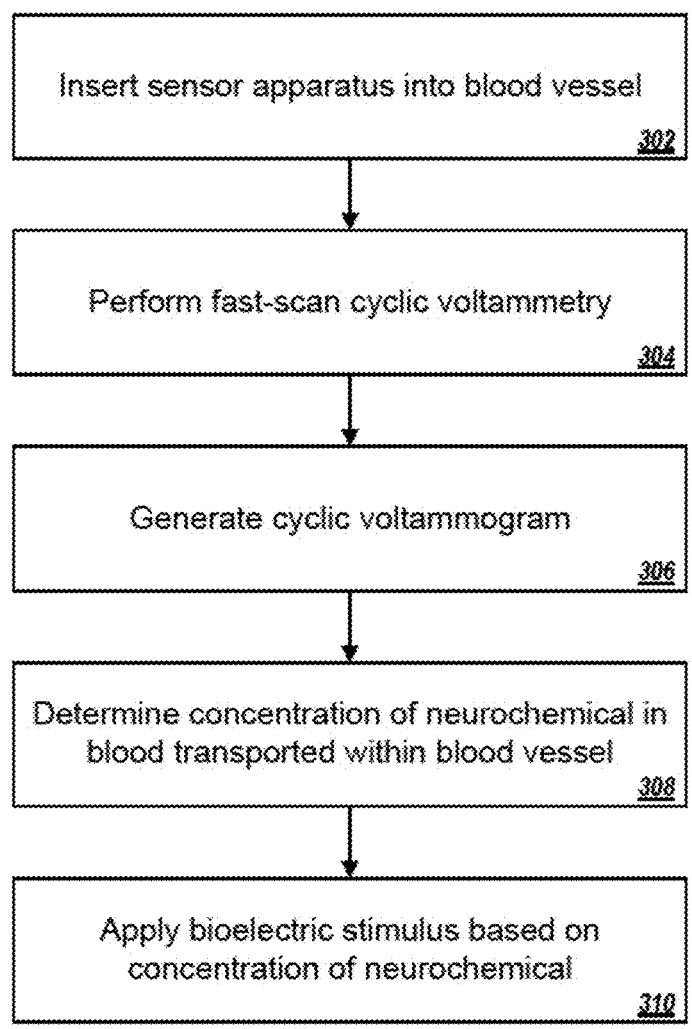
FIG. 3 is a flowchart of a process for measuring a level of neurochemical in the bloodstream of a mammal and applying a bioelectric stimulus based on the measured level of the neurochemical.

FIG. 3 is a flowchart of a process 300 for measuring a level of neurochemical in the bloodstream of a mammal and applying a bioelectric stimulus based on the measured level of the neurochemical. At stage 302, an operator inserts electrodes of a sensor apparatus into the blood vessel of a mammal at or near an end organ that is the target for therapeutic biomolecular changes from the bioelectric therapy. The electrodes may be guided into position within the blood vessel using high-frequency ultrasound techniques, fluoroscopy techniques, magnetic resonance imaging (MRI) techniques, angiography techniques, techniques for measuring the electrical impedance to identify target and large vasculature to avoid, or a combination of multiple guiding techniques. At stage 304, a voltammetry process, e.g., fast-scan cyclic voltammetry, is performed with the sensor apparatus to determine a response to a voltage waveform applied in the bloodstream of the mammal. In some implementations, a DC bias voltage may be applied to facilitate rejuvenation. At stage 306, a voltammetry computing system, e.g., voltammetry computing system 102, uses a signal from the sensor apparatus to generate a voltammogram that characterizes a result of the fast-scan cyclic voltammetry process. At stage 308, the voltammetry computing system determines values of one or more features of the voltammogram and uses theses values to determine a concentration of a neurochemical in the bloodstream at one or more times during the voltammetry process. The concentration of the neurochemical can be estimated using a neurochemical concentration model, e.g., neurochemical concentration model 112 or the models represented by FIGS. 8A and 8B. The voltammetry computing system communicates an indication of the neurochemical concentration to a bioelectric stimulus system, e.g., bioelectric stimulus system 106, which is configured to select a stimulation profile according to the determined neurochemical concentration and none, one, or more other biomarkers. The bioelectric stimulus system then applies the selected stimulation profile at stage 310.

Figure 4:
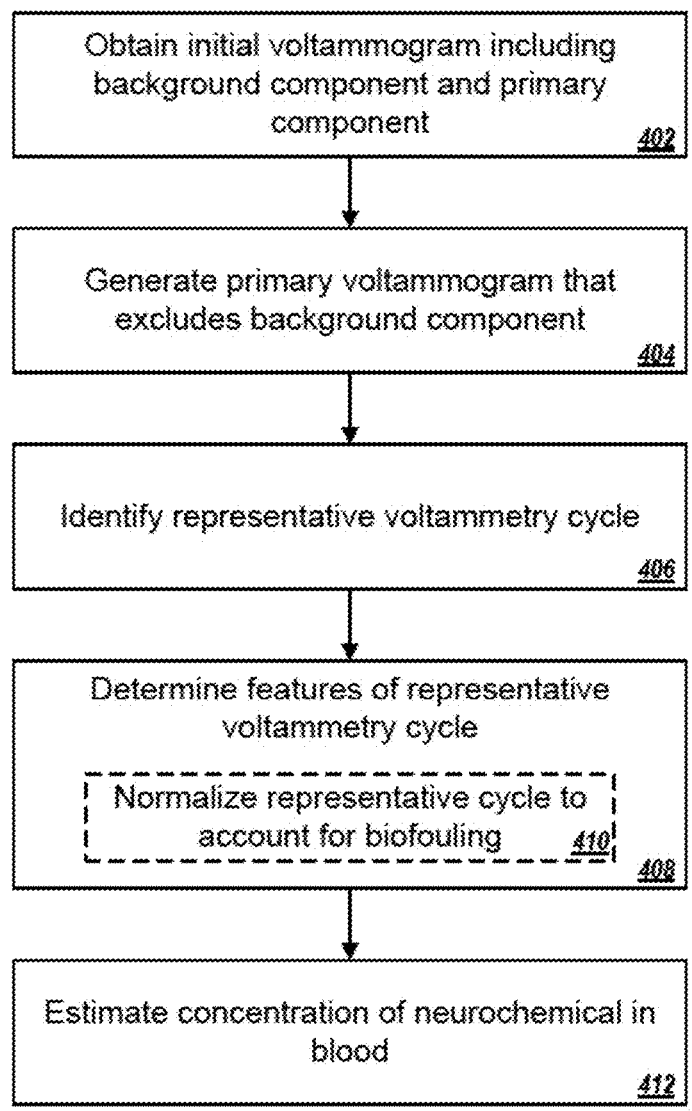
FIG. 4 is a flowchart of an example process for estimating the level of a neurochemical in a volume of blood using a voltammogram that characterizes the result of a fast-scan cyclic voltammetry process.

FIG. 4 is a flowchart of an example process 400 for estimating the level of a neurochemical in a volume of blood (e.g., a bloodstream of a mammal) using a voltammogram that characterizes the result of a fast-scan cyclic voltammetry process. The process 400 can be carried out by a voltammetry computing system, e.g., voltammetry computing system 102.

At stage 402, the system obtains an initial voltammogram characterizing the result of a fast-scan cyclic voltammetry process in which electrodes of a sensing apparatus were at least partially immersed in a volume of blood of a mammal. The initial voltammogram can include both a background component and a primary component. The background component characterizes electrical currents that result in the volume of blood of the mammal substantially independent of the neurochemical during the fast-scan cyclic voltammetry process. The primary component characterizes electrical currents in the volume of blood of the mammal that result from presence of the neurochemical in the volume of blood during the fast-scan cyclic voltammetry process. The initial voltammogram may be a sum of the background and primary components, which are not initially separated from each other.

At stage 404, the VGA engine of the system generates a primary voltammogram that characterizes the primary component of the initial voltammogram to the exclusion of the background component of the initial voltammogram. In some implementations, the VGA engine accesses a pre-stored template of the background component of the initial voltammogram and subtracts the background component from the initial voltammogram in order to separate it from the primary component.

At stage 406, the VGA engine of the system identifies a representative voltammetry cycle from the primary voltammogram. In some implementations, the representative voltammetry cycle is one of the repeated voltammetry cycles that occurred during the fast-scan cyclic voltammetry process. The VGA engine may select one of these cycles as the representative cycle at random or based on one or more quality criteria. For example, a cycle that has sufficiently low noise and is sufficiently similar to other cycles in the voltammogram may be selected. In some implementations, the representative cycle is generated by combining (e.g., averaging) the voltammograms for multiple actual cycles of the voltammetry process. Averaging the actual cycles to create a representative cycle may smooth noise and other insignificant differences among the cycles.

At stage 408, the VGA engine determines values for one or more features of the voltammogram for the representative voltammetry cycle. The features can include a characteristic oxidation potential such as the peak oxidation voltage, a characteristic reduction potential such as a peak reduction voltage, an area under a characteristic oxidation wave in the voltammogram, an area under a characteristic reduction wave in the voltammogram, a full width of the characteristic oxidation or reduction waves, a phase (e.g., waveform location) of the peak oxidation or reduction voltages, or a combination of these and/or other features. In some implementations, the levels of multiple neurochemicals in blood may be estimated by determining feature values of the voltammogram and performing principle component analysis to identify components of the voltammogram (e.g., components of the primary voltammogram) that are contributed by each neurochemical.

In some implementations, all or a portion of the voltammogram for the representative voltammetry cycle may be normalized before determining the features values, in order to correct for baseline drift resulting from biofouling of the electrode in blood and/or other abnormalities resulting from the same (stage 410). In some implementations, a peak detector algorithm is used to identify and isolate the characteristic oxidation or reduction waves from the rest of the representative voltammetry cycle, thereby minimizing the impact on the neurochemical measurement caused by drift of the whole waveform due to biofouling, electrode dissolution, or other changes at the electrode. In some implementations, a bandpass filter can isolate a component of the representative voltammetry cycle having frequencies in the range of about 0.01 Hz to about 2 kHz. The bandpass filter can be applied to reduce/eliminate high frequency noise and low frequency drift. A notch filter reducing/eliminating frequency components from about 10 Hz to about 300 Hz may also be applied to minimize artifact created by potential biological interferents that also contribute to the initial voltammogram. In some implementations, the normalizing can include determining a mean fit of the drift of the resulting current in the voltammogram of the representative cycle to a line that will be set as the zero value, thereby removing the drift component resulting from biofouling of the electrode. Other signal processing techniques that may be applied to the voltammogram of the representative cycle in order to normalize the voltammogram and correct for noise resulting from biofouling of the electrode is to perform wavelet denoising, non-parametric denoising/regression, parametric regression, and/or principal component analysis.

At stage 412, the voltammetry computing system uses a neurochemical concentration model to determine an estimated measurement of the concentration of a neurochemical in a sample of blood based on the features values of the voltammogram for the representative voltammetry cycle. The neurochemical concentration model may be trained based on empirical data that correlates values of a particular voltammogram feature, or values of particular combinations of voltammogram features, with concentrations of a neurochemical in blood. The system provides the feature values as input to the neurochemical model and obtains as output an indication of the level (e.g., concentration) of neurochemical in the blood.

FIGS. 5A-5E show a series of voltammogram plots 500, 506, 512, 518, and 530 that can be generated and analyzed by a voltammetry computing system to estimate a level of neurochemical in a volume of blood of a mammal. FIG. 5A shows an original (i.e., initial) voltammogram that includes both a background and primary component resulting from a fast-scan cyclic voltammetry process. FIG. 5B shows a background-subtracted cyclic voltammogram 506 (i.e., a primary cyclic voltammogram) in which the background component of the voltammogram has been removed. To remove jitter and noise in the voltammogram 506, an averaged background-subtracted cyclic voltammogram 512 is shown in FIG. 5C, which is subsequently used as the representative cycle for analysis of the estimated level of neurochemical in the volume of blood. In some implementations, the system may process the initial voltammogram to identify features representative of neurochemical concentrations, rather than first removing the primary component and isolating the background component. However, first removing the background component can be advantageous due to the relative scale of electrical currents contributed by the primary component vs. the background component. The primary component currents can be orders of magnitude smaller than the background component currents, thereby making it more difficult to discriminate the bounds in the second derivative.

Figure 5D:
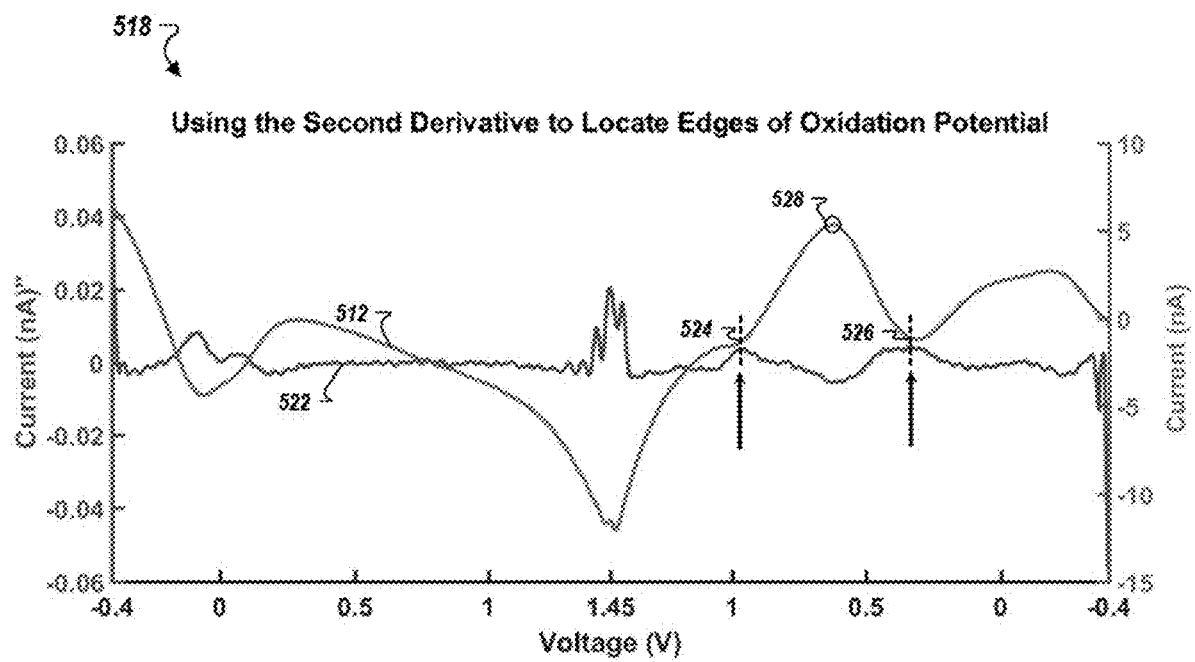

FIG. 5D shows in greater detail the averaged background-subtracted cyclic voltammogram 512 (unfolded) and a plot of the second derivative 522 of the averaged background-subtracted cyclic voltammogram 512. The VGA engine may calculate the second derivative 522, for example, to determine the bounds of a characteristic oxidation wave or a characteristic reduction wave that occurs in the representative cycle, e.g., in the averaged background-subtracted cyclic voltammogram 512. The characteristic oxidation wave appears in the portion of the voltammogram that corresponds to the second phase of a voltammetry cycle in which the applied voltage is ramped down from the peak voltage to the lower voltage. The characteristic reduction wave, in contrast, appears in the portion of the voltammogram that corresponds to the first phase of the voltammetry cycle in which the applied voltage is ramped up from the lower voltage to the peak voltage. The characteristic oxidation wave includes the peak electrical current during oxidation of the electrochemical in the second phase of the voltammetry cycle. The characteristic reduction wave includes the peak electrical current during reduction of the electrochemical in the first phase of the voltammetry cycle. The peak oxidation and reduction waves can be identified by manual inspection or automated means. For example, the VGA engine may determine the second derivative of the representative cycle of the primary voltammogram. The times 524 and 526 at which peaks in the second derivative occur can be selected as the starting and ending times of the peak oxidation or reduction waves.

Figure 5E:
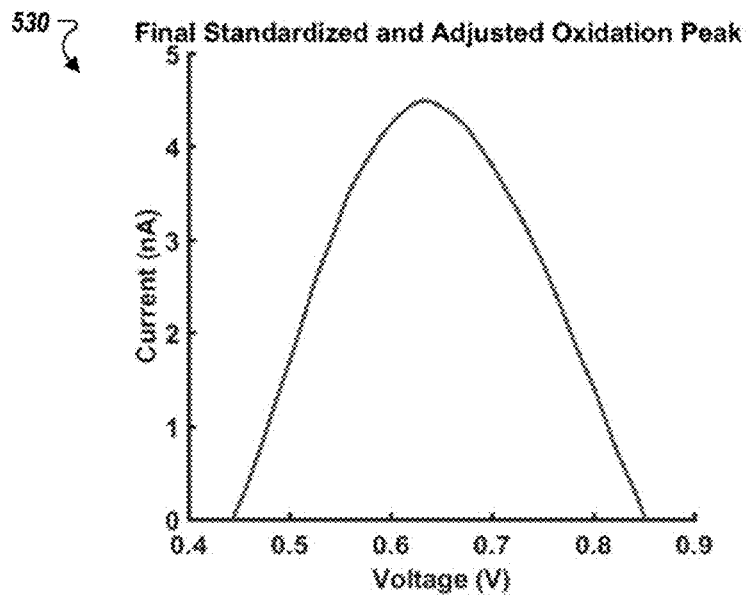

In some implementations, the peak oxidation or reduction wave is normalized to remove the effects of drift as a result of biofouling of the electrodes in blood. FIG. 5E shows an example normalized characteristic oxidation wave derived from the averaged background-subtracted cyclic voltammogram 512 of FIGS. 5C and 5D. The VGA engine in a voltammetry computing system can then determine feature values of the normalized characteristic oxidation wave, and/or feature values of the normalized characteristic reduction wave, to use in estimating the level of a neurochemical in the volume of blood of the mammal. In some implementations, the feature value is a peak electrical current of the normalized characteristic oxidation wave. In some implementations, the feature value is a peak electrical current of a rectified and normalized characteristic reduction wave.

EXAMPLE 1

In a first study, the feasibility of using fast scan cyclic voltammetry (FSCV) to measure norepinephrine levels directly from blood was examined. Norepinephrine is a neurochemical relevant to end-organ function. FSCV is a technique for measuring electroactive neurochemicals in the central nervous system with high temporal and high spatial resolution. The results demonstrate that while detecting the electroactive neurochemical norepinephrine in blood is more challenging than obtaining the same FSCV measurements in a buffer solution due to biofouling of the electrode, it is feasible to utilize a minimally invasive FSCV electrode to obtain neurochemical measurements in blood.

In order to better understand the impact exposure to blood may have on fast-scan cyclic voltammetry (FSCV) measurements taken by carbon fiber microelectrodes (CFMs), here FSCV measurements of known concentrations of NE added to heparinized blood drawn from a pig are directly compared to FSCV measurements taken at the same concentration of NE in a tris buffered saline (TBS) solution.

Methods and Materials

All chemicals were purchased from SIGMA-ALDRICH (St. Louis, Mo.). TBS consisted of 150 mM sodium chloride and 12 mM trizma base dissolved in distilled deionized (DI) water. pH was adjusted to 7.4 using a 10 M hydrochloric acid solution. A 10 mM NE stock solution was prepared by dissolving NE hydrochloride in DI water, and a two-step dilution from the stock to 100 µM to final desired concentrations was performed in TBS or blood. Blood was collected from the femoral vein in anesthetized domestic swine, and heparinized within the syringe using 5 mL of heparin for 30 mL of blood. Blood was kept at room temperature to allow it to equilibrate to the temperature of the TBS; blood measurements were made within one hour of blood being drawn.

Carbon fiber microelectrodes (CFMs) were fabricated by sealing the junction of a carbon fiber and a silica tube with polyamic acid (polyamide) and using nitinol (alloy of nickel and titanium) as an extension wire. A single polyacrylonitrile-based carbon fiber (7 µm diameter; CYTEC, Woodland Park, N.J.) was aspirated into a silica tube (100 µm diameter; POLYMICRO TECHNOLOGIES, Phoenix, Ariz.) and a sealed tip was formed by curing polyamide. This assembly was connected to a nitinol extension wire using a mixture of 50% polyamide and 50% silver powder (STREM CHEMICALS, Newburyport, Mass.). The combined assembly was covered using polyamide tubing (300 µm diameter; SMALL PARTS INC., Logansport, Ind.), and sealed at the tip by curing polyamide. The exposed carbon fiber was cut to a final length of approximately 100 µm by cleaving with a scalpel blade.

Experiments were performed in a beaker utilizing the Universal Electrochemical Instrument (University of North Carolina, Chapel Hill, N.C.) to produce FSCV waveforms and to collect the resulting cyclic voltammograms (CVs). CFMs were pre-conditioned using a holding potential of −0.4 V that was then ramped to 1.3 V and back to −0.4 V at 400 V/s vs silver chloride (Ag/AgCl) reference in the TBS solution for fifteen minutes at 30 Hz prior to beginning the experiments [See K. T. Kishida, I. Saez, T. Lohrenz, M. R. Witcher, A. W. Laxton, S. B. Tatter, J. P. White, T. L. Ellis, P. E. M. Phillips, P. R. Montague, "Subsecond dopamine fluctuations in human striatum encode superposed error signals about actual and counterfactual reward," Proceedings of the National Academy of Sciences, vol. 113, pp. 200-205, January 2016]. The experiments were performed using similar FSCV parameters, but at 10 Hz instead of 30 Hz. Separate beakers containing TBS with 0, 0.1, 0.5, and 1 µM NE, respectively, were prepared. Similarly, separate beakers containing blood with 0, 0.1, 0.5, 1, 5, 10, and 15

μM NE added were also prepared. The highest concentrations (5, 10, and 15 μM) of NE were used in anticipation of difficulties detecting NE in blood. FSCV measurements were performed for three minutes in each beaker starting with the lowest concentration of NE in TBS and ending with the highest concentration of NE in TBS, and then tested in the same order in blood using the same set of electrodes. Scanning electron microscope (SEM) images of a subset of electrodes were collected before experiments, after recordings in TBS, and after recordings in blood.

The current measured during an FSCV scan consists of a background component generated by capacitive current and faradaic current generated by electrochemical reactions unrelated to the analyte of interest, as well as faradaic current resulting from reduction or oxidation reactions involving the analyte of interest, NE. For simplicity, this specification refers to 'background currents' as the capacitive current plus any faradaic current generated by electrochemical reactions unrelated to NE oxidation/reduction, and current resulting from the oxidation/reduction of NE as faradaic current. To minimize the impact of capacitive current on the measurements, as per standard practice CVs were first collected in solutions without NE and subtracted from CVs collected in solutions containing NE in order to obtain the background subtracted cyclic voltammograms (BSCV). The BSCV therefore provides an estimate of the faradaic current resulting from reduction and oxidation reactions involving NE. Utilizing the BSCV, the characteristic oxidation and reduction currents for NE became visibly apparent.

Two methods of quantifying the oxidation/reduction currents from the BSCV were used. First, the peak current amplitude for the characteristic oxidation and reduction humps (peak oxidation and reduction waves) in the BSCV were noted (i.e. the faradaic current), and the voltage location of the peak current amplitude for the oxidation hump was identified. Second, the area under the CV, and the areas under the oxidation and reduction peaks in the BSCV were calculated via trapezoidal integration (See Table 1). For the BSCV in blood, the oxidation and reduction humps were often superimposed on an underlying low-frequency drift apparently caused by progressive biofouling of the electrodes. To minimize this drift, additional manipulation was employed. The beginning and the end of the oxidation and reduction potential "humps" were identified, and a line was drawn from the beginning of the hump to the end of the hump to correct for drift. Only the area under the hump above this correction line was measured to isolate the signal from drift. These isolated humps (i.e., normalized peak oxidation and reduction waves) were also used to collect peak amplitudes corrected for drift.

Results

Figure 6A:
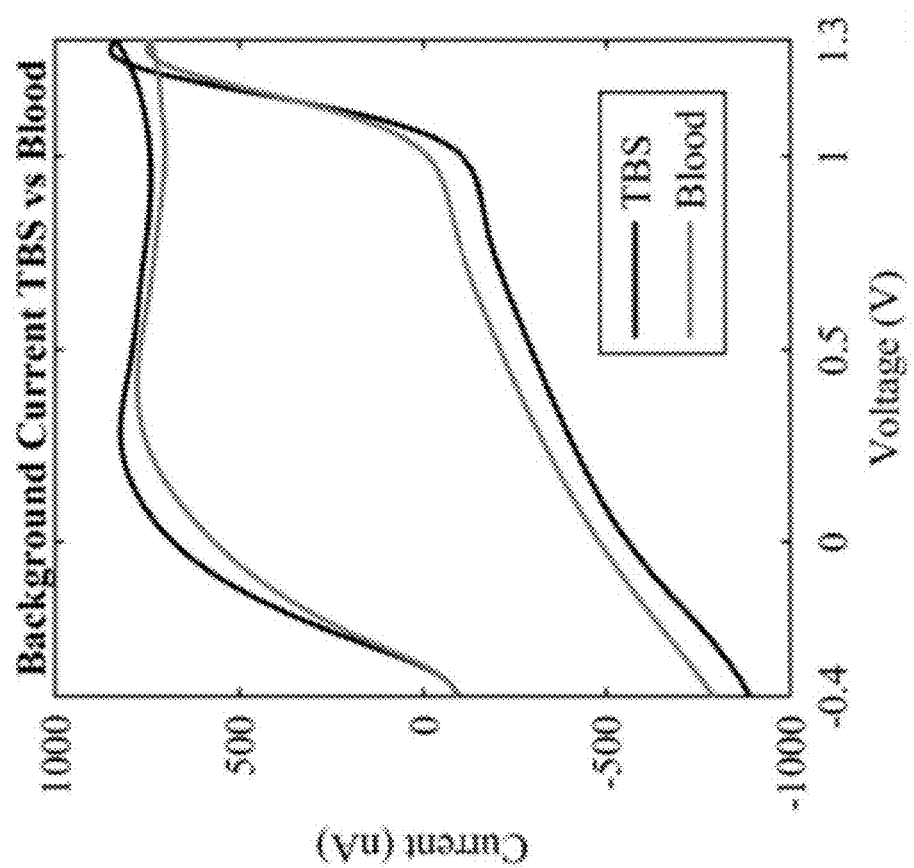
FIGS. 6A and 6B are static voltammograms for TBS and blood solutions, respectively.
Figure 6B:
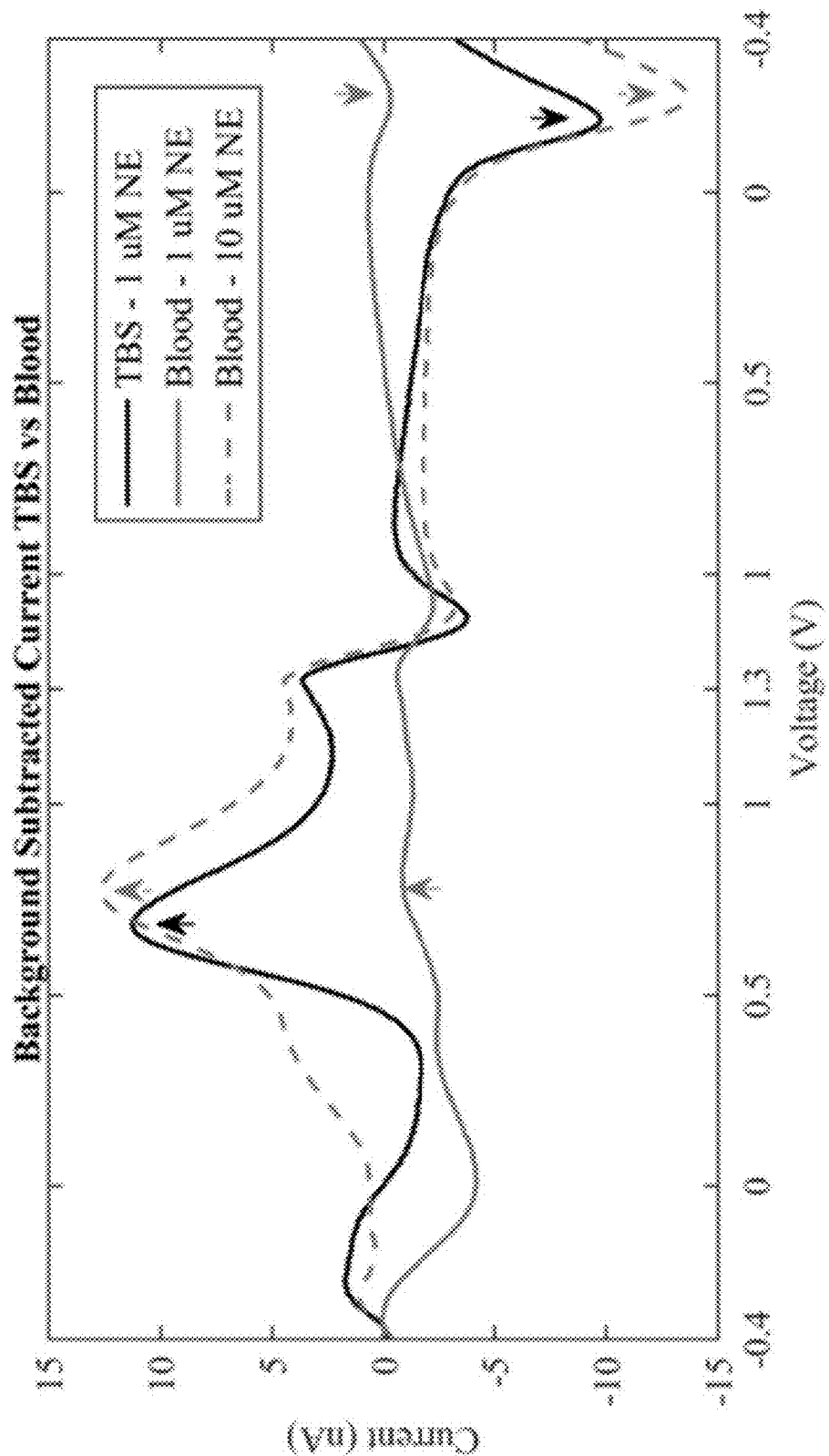
Figures 7A, 7B, 7C, 7D:
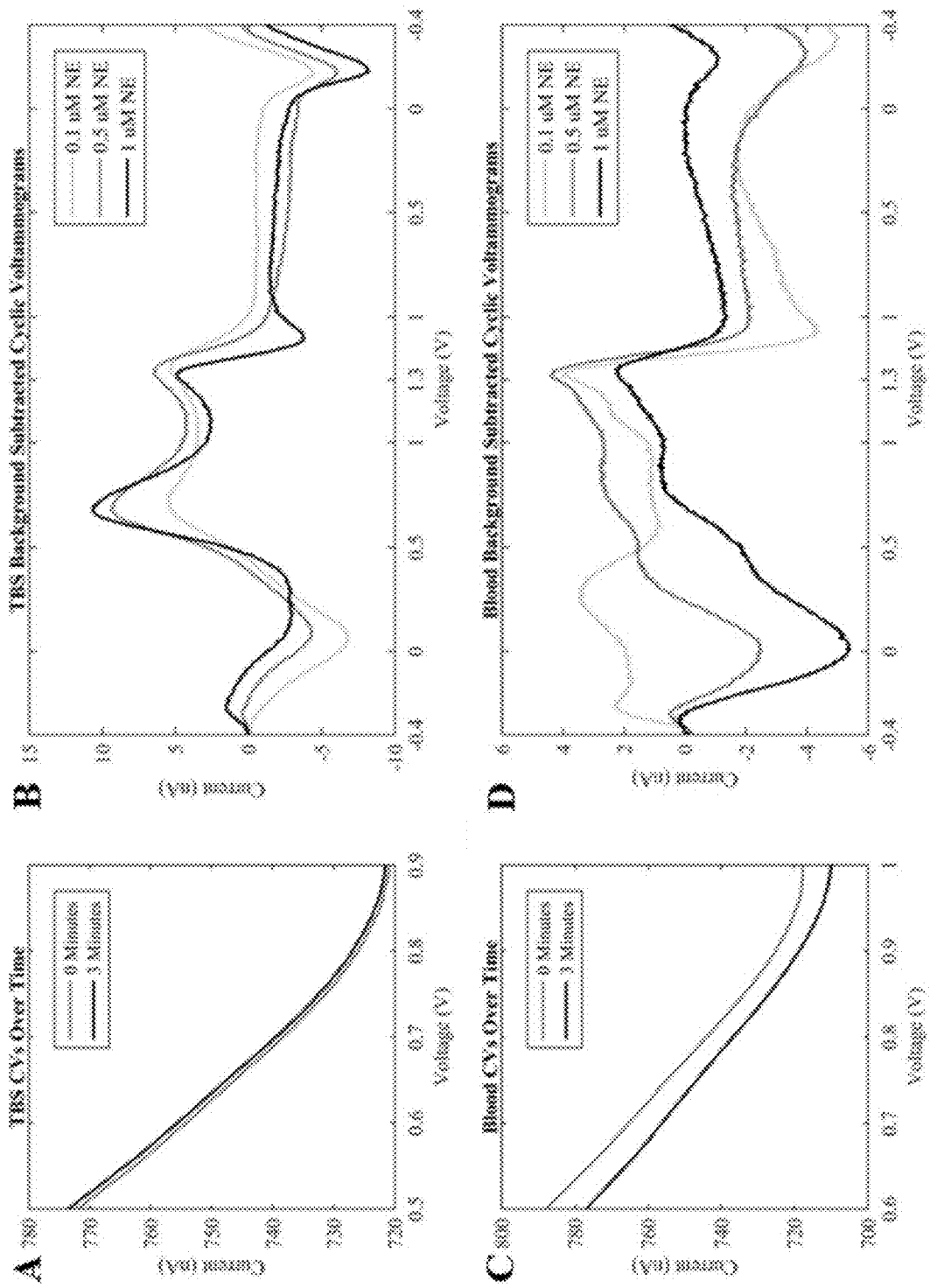
FIGS. 7A-D show static voltammograms for TBS and blood over time.

Changes in the Voltammogram: Immediately upon the start of recording, CVs collected in heparinized blood were noticeably different in overall shape as compared to recordings in TBS (FIG. 6A). The voltage location of the oxidation and reduction potentials measured in blood shifted approximately +100 mV and −60 mV, respectively, from their locations in TBS (FIG. 6B). Finally, there was an approximate 12% overall decrease in capacitive, non-faradaic current as calculated by the area under the full CV (Table 1). Over the course of recording for three minutes, the overall amplitude of the CV in blood shifted approximately ten nA (FIG. 7C).

Figures 8A, 8B:
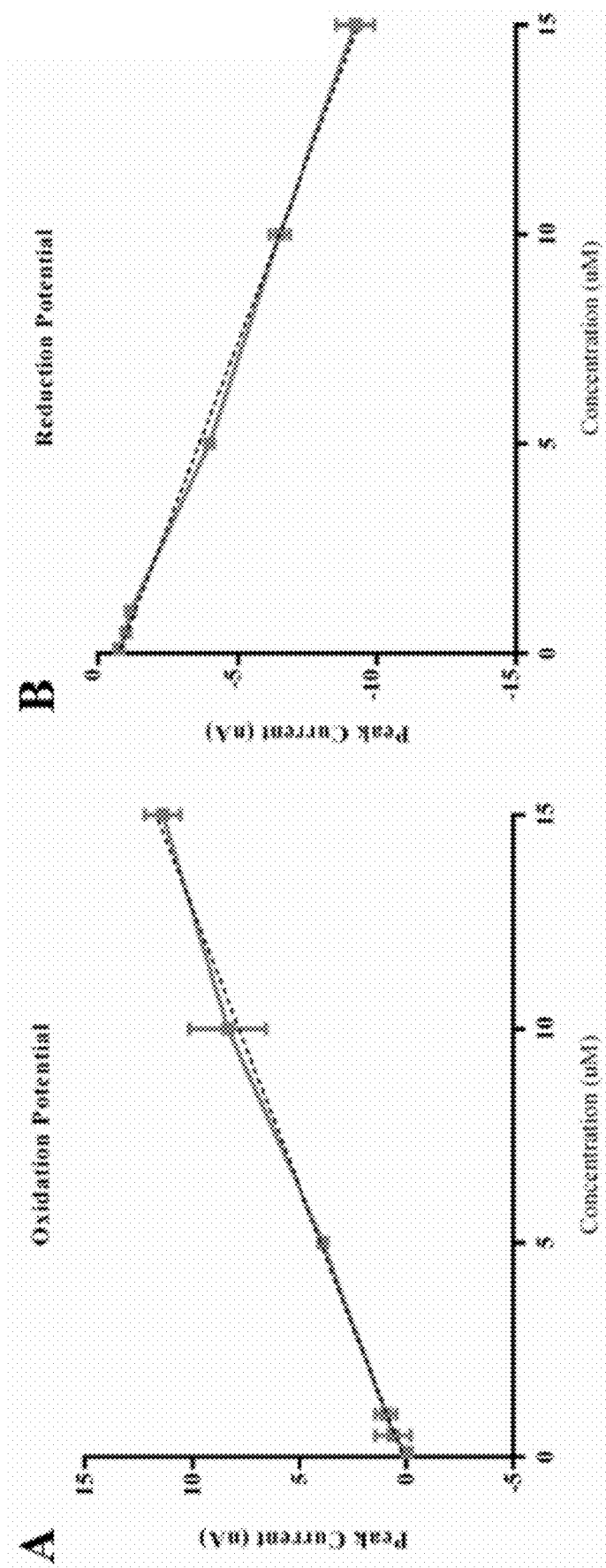
FIGS. 8A and 8B show calibration curves to NE at carbon-fiber microelectrodes in blood.

Calibration to Norepinphrine: A typical representation of a BSCV for a NE signal, measured in TBS, can be found in FIGS. 6A-6B. The oxidation and reduction peak signals, found at 0.67 V and −0.2V respectively, are visually evident. For the same concentration in blood using the same CFMs, the oxidation peak (now at 0.77V) and the reduction peak (now at −0.26V) are less obvious, but still visible. Visually apparent oxidation and reduction peaks were obtained at concentrations 5 μM NE and above in blood (FIG. 6B). A summary of the CV characteristics, peak currents and integrals, can be found in Table 1. Finally, a clear linear correlation between concentration and obtained current for both the oxidation and reduction potentials of NE was evident in blood after employing our simple ad-hoc signal processing method (FIGS. 8A-8B).

TABLE 1

Cyclic Voltammogram Characteristic Comparison TBS vs Blood[a]

| Characteristic | TBS Peak (nA) | Blood Peak (nA) | TBS Integral (nA * V) | Blood Integral (nA * V) |
|---|---|---|---|---|
| Background Current | 763.1 ± 55.9 | 721.7 ± 31.6 | 473,800 ± 37,525 | 412,310 ± 24,644 |
| Oxidation Current[b] | 10.7 ± 1.5 | −0.7 ± 2.3 | 989 ± 38.5 | 84.7 ± 9.7 |
|  | 10.9 ± 0.6 | 1.2 ± 0.1 |  |  |
| Reduction Current[b] | −8 ± 4.6 | −1 ± 2.3 | −329.5 ± 138.4 | −84.4 ± 30 |
|  | −6.1 ± 2.2 | −1.4 ± 0.3 |  |  |

Table 1 includes the data collected from the 1 uM norepinephrine CVs shown in FIG. 6. All values are the mean and standard deviation of data for 4 electrodes. Data above is without ad-hoc correction for drift, and below is with ad-hoc correction.

Figure 9A:
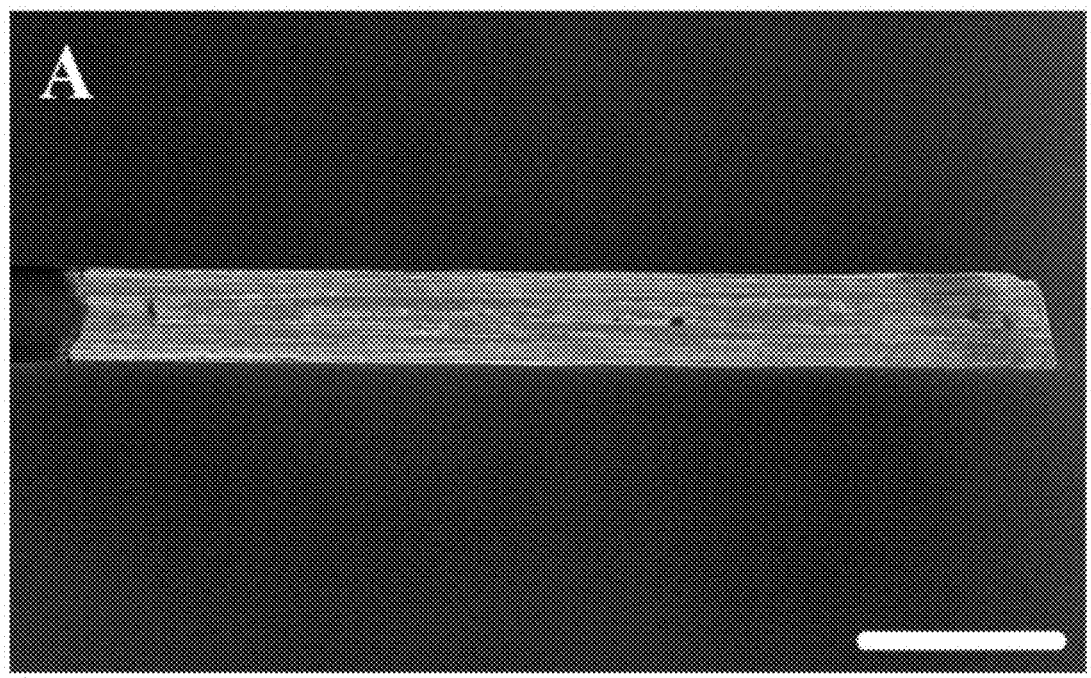
FIGS. 9A and 9B show images of scanning electron micrographs of carbon-fiber microelectrodes (CFM) before and after fast-scan cyclic voltammetry (FSCV) in whole heparinized blood.
Figure 9B:
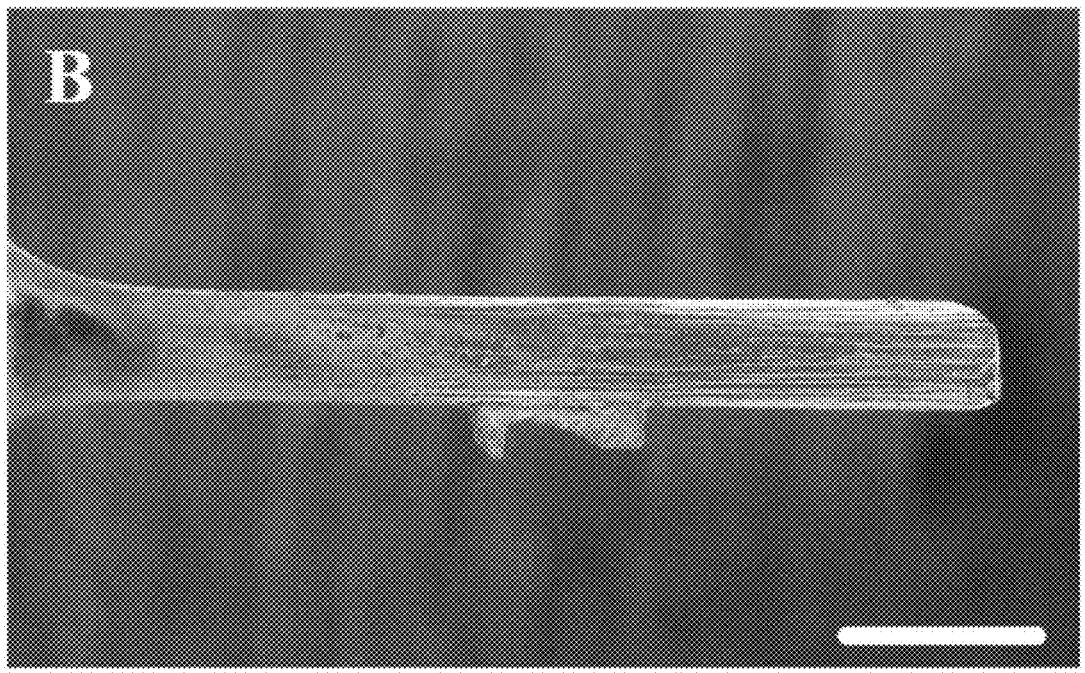

Scanning Electron Microscopy: Comparison of the SEM images before recordings and after use in TBS showed no apparent difference. Comparison after use in TBS and after use in blood showed a coating that preferentially covered the surface of the CFM near the interface between the insulation, polyamide, and the electroactive surface area, carbon fiber (FIG. 9B).

Discussion

Biofouling at the Surface of the Carbon Fiber Microelectrode: The immediate and long-term changes to the CV, sensitivity to NE, and surface of the electrode as visualized by SEM all support the conclusion that blood produces biofouling at the surface of CFMs used for FSCV. The effect of biofouling could be explained in two ways that are not necessarily mutually exclusive. First, the layer of biofouling may increase the impedance that must be overcome to result in application of the expected voltage at the working electrode. For example, if the peak voltage is set to 1.3V, the actual voltage exhausted across the working electrode may only be 1.2V, as additional voltage is lost across the impedance of the layer of biofouling. This could in turn change the shape of the CV, since the shape of the CV is known to change when using different potential ranges [See P. Takmakov, M. K. Zachek, R. B. Keithley, P. L. Walsh, C. Donley, G. S. McCarty, R. M. Wightman, "Carbon microelectrodes with a renewable surface," ACS Analytical Chemistry, vol. 82, pp. 2020-2028, February 2010; R. B. Keithly, P. Takmakov, E. S. Bucher, A. M. Belle, C. A. Owesson-White, J. Park, R. M. Wightman. "Higher sensitivity dopamine measurements with faster-scan cyclic voltammetry," Anal. Chem., vol. 83, pp. 3563-3571, May 2011]. This could also explain the shift in location of the oxidation and reduction peaks in blood compared to those in TBS; in effect the FSCV system would record that the peak oxidation current was obtained at 0.77V, when the voltage drop across the biofouling limited the effective voltage at the working carbon fiber electrode to 0.67V. The observed 13 percent decrease in measured capacitive current in the CV when placed in blood is consistent with this hypothesis. Second, biofouling may block sites at the electrode surface for adsorption of NE and inhibit diffusion to the surface of the electrode. Blocking sites for adsorption would decrease faradaic currents [See C. W. Atcherly, N. D. Laude, K. L. Parent, M. L. Heien, "Fast-scan controlled-adsorption voltammetry for the quantification of absolute concentrations and adsorption dynamics," ACS Langmuir, vol. 29, pp. 14885-14892, November 2013]. Loss due to blocked sites for neurochemical adsorption may explain why the capacitive current decreased by only 13% in blood compared to TBS, whereas the oxidation faradaic current decreased by 92% in blood compared to TBS.

Rejuvenation and Signal Processing: Further optimization may be achieved through advanced signal processing. Note in Table 1 that measurement of the oxidation peak in blood directly from the BSCV gives a negative signal, whereas correcting for drift and isolating the oxidation hump in ad-hoc fashion gives a positive signal correlated with concentration down to 0.1 micromolar. Also worth noting is that the standard deviation drops an order of magnitude for blood. The effect of this drift on multiple concentrations of NE in blood can be found in FIG. 7D. Additional or alternative signal processing techniques may also be used to determine feature values of a representative cycle of a primary voltammogram such as principle components regression and/or wavelet analyses to use the entire waveform to quantify faradaic changes [See M. L. Heien, M. A. Johnson, R. M. Wightman, "Resolving neurotransmitters detected by fast-scan cyclic voltammetry," Anal. Chem., vol. 76, pp. 5697-704, October 2004; R. B. Keithly, R. M. Wightman, "Assessing principal component regression prediction of neurochemicals detected with fast-scan cyclic voltammetry," ACS Chem. Neurosci., vol. 2, pp. 514-525, June 2011], as well as techniques to automatically correct for drift, minimize noise, and isolate faradaic components. Secondly, applying a higher peak voltage at a faster frequency for a short period of time has been shown to "rejuvenate" the surface of CFMs and temporarily remove biofouling [See P. Takmakov, M. K. Zachek, R. B. Keithley, P. L. Walsh, C. Donley, G. S. McCarty, R. M. Wightman, "Carbon microelectrodes with a renewable surface," ACS Analytical Chemistry, vol. 82, pp. 2020-2028, February 2010]. The rejuvenation protocol can be applied to CFMs in blood to obtain improved sensitivity recordings in an intermittent fashion. Third, different waveforms can be used to optimize recorded FSCV signal. Greater sensitivity to electroactive neurochemicals has previously been demonstrated by scanning to higher anodic potentials [See M. L. Heien, P. E. Philips, G. D. Stuber, A. T. Seipel, R. M. Wightman, "Overoxidation of carbon-fiber microelectrodes enhances dopamine adsorption and increases sensitivity," Analyst, vol. 128, pp. 1413-1419, December 2003], as well as using faster scan rates [See R. B. Keithly, P. Takmakov, E. S. Bucher, A. M. Belle, C. A. Owesson-White, J. Park, R. M. Wightman. "Higher sensitivity dopamine measurements with faster-scan cyclic voltammetry," Anal. Chem., vol. 83, pp. 3563-3571, May 2011]. Finally, locating the electrode closer to the source of the NE should minimize the impact of dilution in circulating blood, which could increase the concentration of NE being measured, thus reducing the sensitivity requirement. A relevant source of NE in the viscera is the kidneys, so one may use a catheter system to deliver CFMs to the renal vein or artery to increase the concentration of NE measured.

Conclusions

Although biofouling in blood was found to dramatically reduce the sensitivity of the FSCV electrode to NE both immediately and over time, oxidation/reduction peaks characteristic of NE were still observable at concentrations 1-2 orders of magnitude more than concentration changes anticipated to be relevant to ANS neuromodulation therapies when measured in circulating blood.

EXAMPLE 2

Bioelectronic medicines are an emerging area focused on treating diverse disease/disorders using precise, minimally invasive electrical stimulation to modulate autonomic nerves controlling end-organ function. Bioelectronic medicines may benefit from quantifiable, real-time feedback of stimulation. Vagus nerve stimulation (e.g., using bioelectric stimulus system 106) can cause a variety of physiological changes throughout the body. Stimulation of the vagus nerve can also slow breathing to a halt, which causes the Hering-Breuer Reflex (HBR) to initiate, restoring breathing to normal [See Siniaia, M. S., Young, D. L., & Poon, C.-S. (2000). Habituation and desensitization of the Hering-Breuer reflex in rat. Journal of Physiology, 479-491]. Activation of the HBR could be expected to be accompanied by sympathetic activation and release of norepinephrine. Fast scan cyclic voltammetry (FSCV) is an electrochemical technique that can be used in the central nervous system to measure norepinephrine with subsecond and submillimeter precision [See Park, J., Takmakov, P., & Wightman, R. M. (2011). In Vivo Comparison of Norepinephrine and Dopamine Release in Rat Brain by Simultaneous Measurements with Fast-Scan Cyclic Voltammetry. Journal of Neurochemistry, 932-944].

Methods

This study used homemade nerve cuffs, adapted from [See Childs, J. E., Alvarez-Dieppa, A. C., McIntyre, C. K., & Kroener, S. (2015). Vagus Nerve Stimulation as a Tool to Induce Plasticity in Pathways Relevant for Extinction Learning. Journal of Visualized Experiments], to stimulate the vagus nerve near the carotid bifurcation in order to elicit the HBR. MAYO CLINIC developed WINCS HARMONI was used to apply FSCV at the tip of a carbon fiber microelectrode (CFM) implanted in the cortex of the kidney near the renal vein. Desipramine, a norepinephrine reuptake inhibitor, was injected intraperitoneal in order to pharmacologically verify that the evoked signal was norepinephrine.

Results

Figure 10:
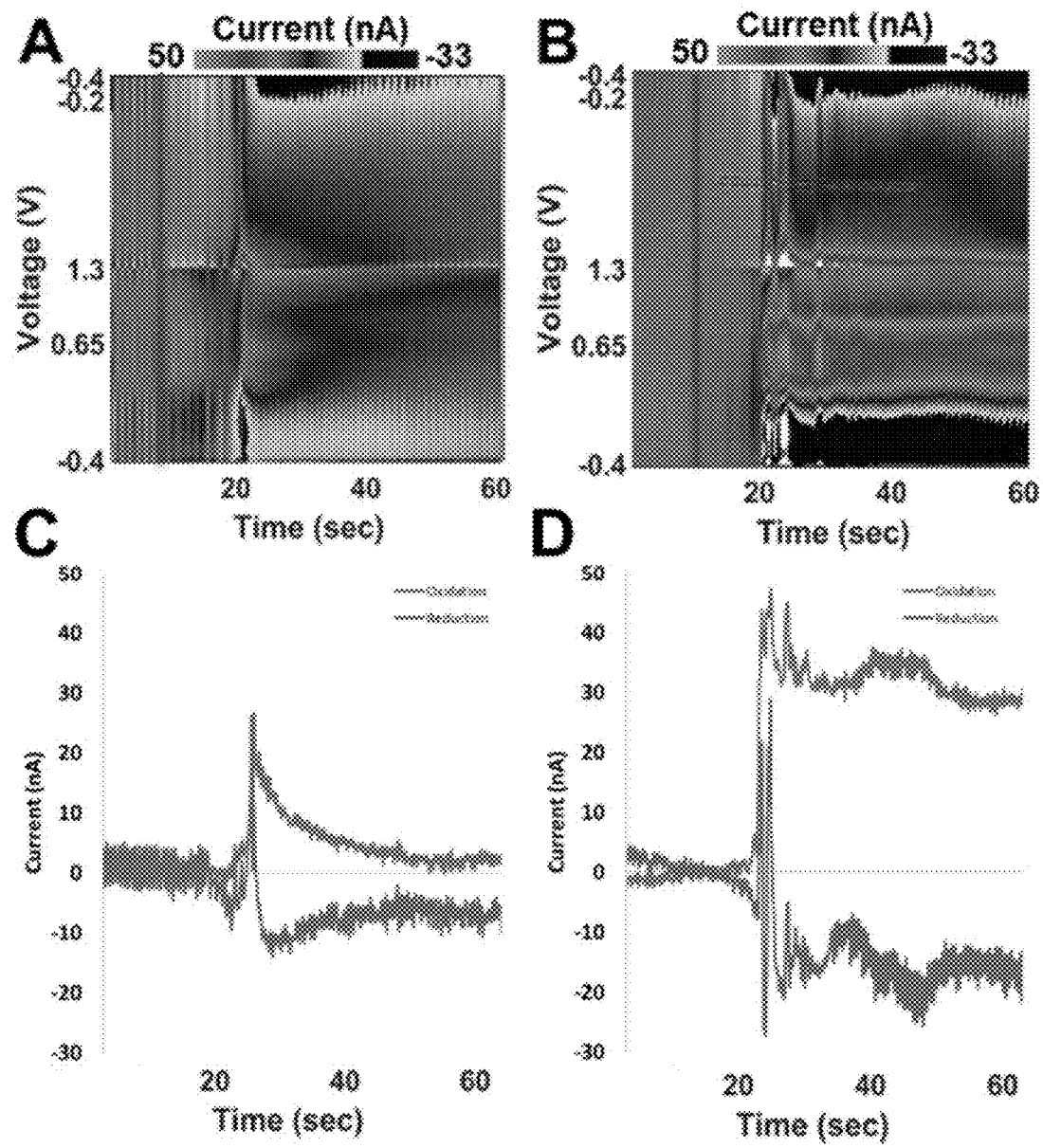
FIG. 10 shows FSCV recordings in the cortex of the kidney during vagus nerve stimulation before and after i.p. injection of desipramine, a norepinephrine reuptake inhibitor. The reuptake inhibitor lengthens and strengthens the characteristic FSCV signal of norepinephrine, thereby validating neurochemical specificity of the technique. The top row shows FSCV gradient plots. The x-axis is time, y-axis is voltage, and color represents current. The bottom row shows versus time plots. The black trace (i.e., the predominantly top trace in the images) is the characteristic oxidation current and the green trace (i.e., the predominantly bottom trace in the images) is the characteristic reduction current.

Vagus nerve stimulation resulted in cessation of breathing and activation of HBR as confirmed by reinstatement of breathing during stimulation. FSCV measurement of catecholamine release was recorded approximately fifteen seconds following beginning of stimulation and coincided with reinstatement of breathing. Injection of desipramine caused an apparent increase in the amplitude and duration of the measured FSCV signal, indicative of norepinephrine measurement [FIG. 10].

Conclusions

FSCV can be used to measure the neurochemical correlates of the HBR elicited by vagus nerve stimulation in real-time at the kidney. These results provide support for the use of FSCV for measurement of biomarkers of bioelectronic medicines therapy.

Computing Systems

Figure 11:
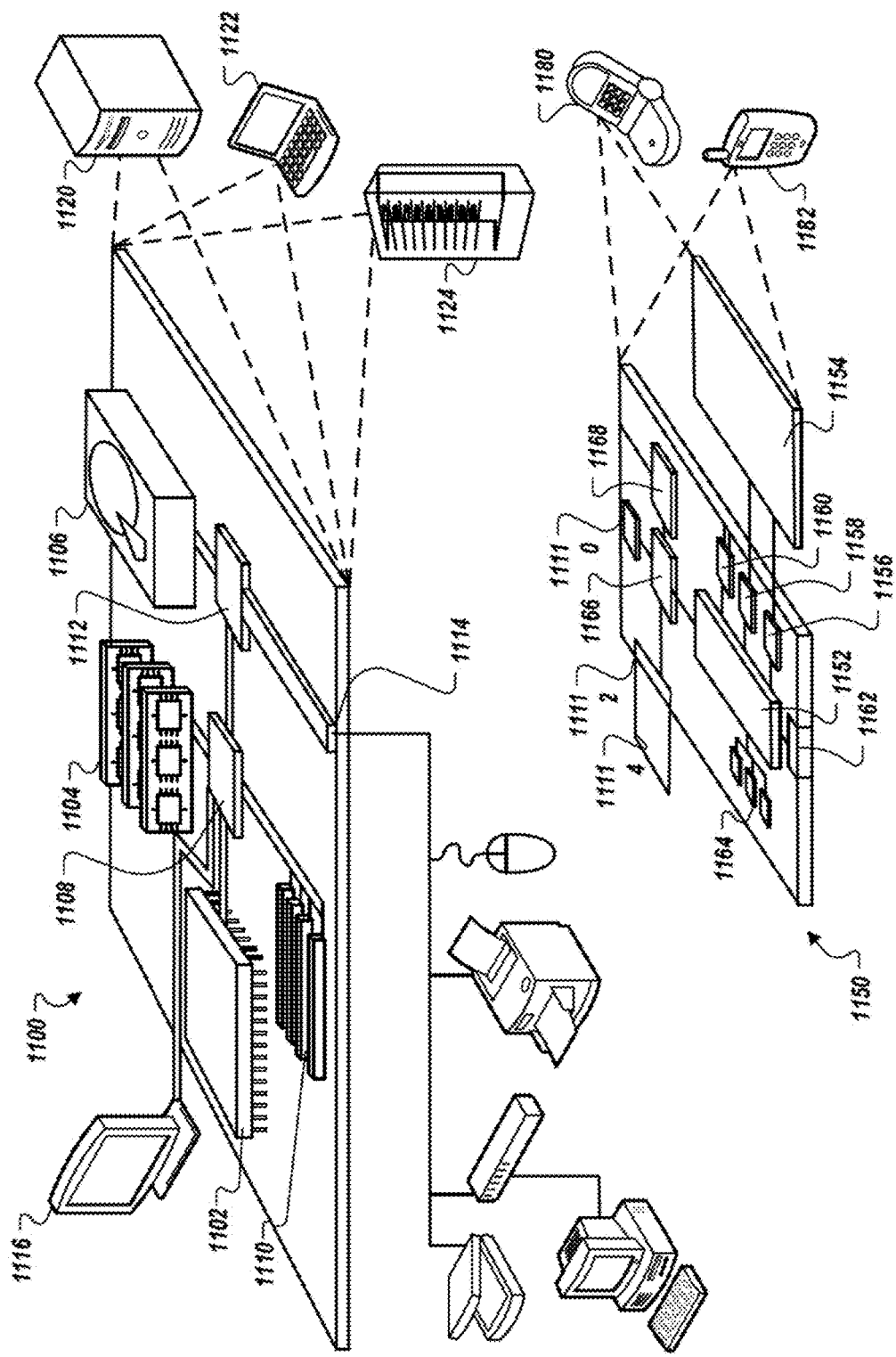
FIG. 11 shows an example of a computing device and a mobile computing device that can be used to implement particular techniques described herein.

FIG. 11 shows an example of a computing device 1100 and a mobile computing device that can be used to implement the techniques described herein. For example, the voltammetry computing system 102 and/or the bioelectric stimulus system 106 may include a combination of software and hardware like that described with respect to FIG. 11. The computing device 1100 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1104 stores information within the computing device 1100. In some implementations, the memory 1104 is a volatile memory unit or units. In some implementations, the memory 1104 is a non-volatile memory unit or units. The memory 1104 may also be another form of computer-readable medium, such as a magnetic or optical disk.

The storage device 1106 is capable of providing mass storage for the computing device 1100. In some implementations, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. The computer program product may also contain instructions that, when executed, perform one or more methods, such as those described above. The computer program product can also be tangibly embodied in a computer- or machine-readable medium, such as the memory 1104, the storage device 1106, or memory on the processor 1102.

The high-speed interface 1108 manages bandwidth-intensive operations for the computing device 1100, while the low-speed interface 1112 manages lower bandwidth-intensive operations. Such allocation of functions is exemplary only. In some implementations, the high-speed interface 1108 is coupled to the memory 1104, the display 1116 (e.g., through a graphics processor or accelerator), and to the high-speed expansion ports 1110, which may accept various expansion cards (not shown). In the implementation, the low-speed interface 1112 is coupled to the storage device 1106 and the low-speed expansion port 1114. The low-speed expansion port 1114, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. In addition, it may be implemented in a personal computer such as a laptop computer 1122. It may also be implemented as part of a rack server system 1124. Alternatively, components from the computing device 1100 may be combined with other components in a mobile device (not shown), such as a mobile computing device 1150. Each of such devices may contain one or more of the computing device 1100 and the mobile computing device 1150, and an entire system may be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 may also be provided with a storage device, such as a micro-drive or other device, to provide additional storage. Each of the processor 1152, the memory 1164, the display 1154, the communication interface 1166, and the transceiver 1168, are interconnected using various buses, and several of the components may be mounted on a common motherboard or in other manners as appropriate.

The processor 1152 can execute instructions within the mobile computing device 1150, including instructions stored in the memory 1164. The processor 1152 may be implemented as a chipset of chips that include separate and multiple analog and digital processors. The processor 1152 may provide, for example, for coordination of the other components of the mobile computing device 1150, such as control of user interfaces, applications run by the mobile computing device 1150, and wireless communication by the mobile computing device 1150.

The processor 1152 may communicate with a user through a control interface 1158 and a display interface 1156 coupled to the display 1154. The display 1154 may be, for example, a TFT (Thin-Film-Transistor Liquid Crystal Display) display or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may provide communication with the processor 1152, so as to enable near area communication of the mobile computing device 1150 with other devices. The external interface 1162 may provide, for example, for wired communication in some implementations, or for wireless communication in other implementations, and multiple interfaces may also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 may also be provided and connected to the mobile computing device 1150 through an expansion interface 1172, which may include, for example, a SIMM (Single In Line Memory Module) card interface. The expansion memory 1174 may provide extra storage space for the mobile computing device 1150, or may also store applications or other information for the mobile computing device 1150. Specifically, the expansion memory 1174 may include instructions to carry out or supplement the processes described above, and may include secure information also. Thus, for example, the expansion memory 1174 may be provide as a security module for the mobile computing device 1150, and may be programmed with instructions that permit secure use of the mobile computing device 1150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. The computer program product contains instructions that, when executed, perform one or more methods, such as those described above. The computer program product can be a computer- or machine-readable medium, such as the memory 1164, the expansion memory 1174, or memory on the processor 1152. In some implementations, the computer program product can be received in a propagated signal, for example, over the transceiver 1168 or the external interface 1162.

The mobile computing device 1150 may communicate wirelessly through the communication interface 1166, which may include digital signal processing circuitry where necessary. The communication interface 1166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1168 using a radio-frequency. In addition, short-range communication may occur, such as using a Bluetooth, WiFi, or other such transceiver (not shown). In addition, a GPS (Global Positioning System) receiver module 1170 may provide additional navigation- and location-related wireless data to the mobile computing device 1150, which may be used as appropriate by applications running on the mobile computing device 1150.

The mobile computing device 1150 may also communicate audibly using an audio codec 1160, which may receive spoken information from a user and convert it to usable digital information. The audio codec 1160 may likewise generate audible sound for a user, such as through a speaker, e.g., in a handset of the mobile computing device 1150. Such sound may include sound from voice telephone calls, may include recorded sound (e.g., voice messages, music files, etc.) and may also include sound generated by applications operating on the mobile computing device 1150.

The mobile computing device 1150 may be implemented in a number of different forms, as shown in the figure. For example, it may be implemented as a cellular telephone 1180. It may also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In situations in which the systems, methods, devices, and other techniques here collect personal information (e.g., context data) about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Although various implementations have been described in detail above, other modifications are possible. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A method, comprising:
   inserting a sensing apparatus in a blood vessel of a mammal;
   performing a fast-scan cyclic voltammetry process using the sensing apparatus in the blood vessel of the mammal;
   determining a cyclic voltammogram that characterizes a result of the fast-scan cyclic voltammetry process;
   processing the cyclic voltammogram to determine a concentration of a neurochemical in blood transported within the blood vessel of the mammal, wherein processing the cyclic voltammogram comprises correcting for a low-frequency drift that results in a sustained shift in an amplitude of the cyclic voltammogram relative to an initial amplitude of the cyclic voltammogram at a start of the fast-scan cyclic voltammetry process; and
   applying a bioelectric stimulus to the mammal, wherein the bioelectric stimulus is adjusted based on the concentration of the neurochemical in the blood transported within the blood vessel of the mammal.

2. The method of claim 1, wherein the mammal is a human.

3. The method of claim 1, wherein the neurochemical is norepinephrine.

4. The method of claim 1, wherein:
   the fast-scan cyclic voltammetry process comprises performing a series of voltammetry cycles that each include (i) a first phase in which a voltage of a working electrode of the sensing apparatus is increased in the volume of blood of the mammal from a first voltage to a second voltage and (ii) a second phase in which the voltage of the working electrode is decreased in the volume of blood of the mammal from the second voltage to the first voltage; and
   the cyclic voltammogram characterizes, for each of one or more voltammetry cycles in the series of voltammetry cycles:
   (i) for each of multiple voltages between the first voltage and the second voltage during the first phase of the voltammetry cycle, a level of electrical current measured in the volume of blood when the working electrode was at the voltage, and
   (ii) for each of multiple voltages between the second voltage and the first voltage during the second phase of the voltammetry cycle, a level of electrical current measured in the volume of blood when the working electrode was at the voltage.

5. The method of claim 4, wherein the fast-scan cyclic voltammetry process was performed at a frequency in the range of 1 to 60 voltammetry cycles per second.

6. The method of claim 4, wherein an active portion of the working electrode comprises a carbon-fiber material, wherein the first voltage and the second voltage are each in the range −0.8 Volts to 2.0 Volts.

7. The method of claim 1, wherein a working electrode of the sensing apparatus is located in the blood vessel of the mammal in order to permit measurement of the concentration of the neurochemical in the blood transported within the blood vessel of the mammal.

8. The method of claim 1, wherein a working electrode of the sensing apparatus is a carbon-fiber microelectrode having a diameter in the range 1 to 1000 microns.

9. The method of claim 1, wherein applying the bioelectric stimulus comprises stimulating the autonomic nervous system of the mammal.

10. The method of claim 1, wherein applying the bioelectric stimulus to the mammal comprises applying the bioelectric stimulus to a vagus nerve of the mammal to induce slowed breathing.

11. The method of claim 1, wherein the neurochemical is catecholamine, and applying the bioelectric stimulus to the mammal comprises adjusting stimulus to the vagus nerve of the mammal to control breathing based on a concentration of catecholamine in blood of the mammal.

12. The method of claim 1, wherein correcting for the low-frequency drift comprises using a peak detector algorithm to isolate a characteristic oxidation or reduction waveform from the cyclic voltammogram.

13. The method of claim 1, wherein correcting for the low-frequency drift comprises applying a bandpass filter to the cyclic voltammogram to isolate a component of the cyclic voltammogram in a specified frequency range.

14. The method of claim 13, wherein the specified frequency range is 0.01 Hz to 2 kHz.

15. The method of claim 1, wherein correcting for the low-frequency drift comprises applying a notch filter to the cyclic voltammogram to suppress a component of the cyclic voltammogram in a specified frequency range.

16. The method of claim 15, wherein the specified frequency range is about 10 Hz to about 300 Hz.

17. The method of claim 1, wherein correcting for the low-frequency drift comprises determining a mean fit of the low-frequency drift to a zero-value line.

18. The method of claim 1, wherein correcting for the low-frequency drift comprises normalizing a representative cycle of the cyclic voltammogram to compensate for the low-frequency drift thereby generating a normalized representative cycle, wherein the method comprises determining the concentration of the neurochemical in blood transported within the blood vessel of the mammal based on one or more features derived from the normalized representative cycle.

19. The method of claim 18, wherein the representative cycle of the cyclic voltammogram is generated by averaging a plurality of cycles of the cyclic voltammogram.

20. The method of claim 1, wherein performing the fast-scan cyclic voltammetry process comprises intermittently applying elevated parameters of the fast-scan cyclic voltammetry process for a period of time to mitigate biofouling of the sensing apparatus, wherein the elevated parameters include an elevated peak voltage and an elevated scanning frequency.

\* \* \* \* \*